(12) United States Patent
Insel et al.

(10) Patent No.: US 11,674,963 B2
(45) Date of Patent: Jun. 13, 2023

(54) GPCRS IN CANCER-ASSOCIATED FIBROBLASTS

(71) Applicant: The Regents of the University of California, Oakland, CA (US)

(72) Inventors: Paul A. Insel, San Diego, CA (US); Andrew M. Lowy, San Diego, CA (US); Shu Wiley, Temecula, CA (US); Randall French, San Diego, CA (US); Krishna Sriram, San Diego, CA (US); Cristina Salmeron, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 424 days.

(21) Appl. No.: 16/650,546

(22) PCT Filed: Sep. 27, 2018

(86) PCT No.: PCT/US2018/053104
§ 371 (c)(1),
(2) Date: Mar. 25, 2020

(87) PCT Pub. No.: WO2019/067709
PCT Pub. Date: Apr. 4, 2019

(65) Prior Publication Data
US 2020/0348305 A1 Nov. 5, 2020

Related U.S. Application Data

(60) Provisional application No. 62/563,884, filed on Sep. 27, 2017.

(51) Int. Cl.
*G01N 33/574* (2006.01)

(52) U.S. Cl.
CPC . *G01N 33/57438* (2013.01); *G01N 2333/726* (2013.01)

(58) Field of Classification Search
CPC .................................................. G01N 33/57438
USPC ............................................................ 435/7.1
See application file for complete search history.

(56) References Cited

U.S. PATENT DOCUMENTS

2012/0196764 A1* 8/2012 Zhang .............. G01N 33/57438
435/6.12

FOREIGN PATENT DOCUMENTS

| WO | 2004/040000 A2 | 5/2004 |
| WO | WO 2014/168922 A2 * | 10/2014 |
| WO | 2017/132661 A2 | 8/2017 |

OTHER PUBLICATIONS

Weng et al (Int J Cancer, 2006, 118: 1471-1480).*
Wang et al (MolecularCancer, 2017, 16(61): 1-14).*
Kisfalvi et al (Canc Res, 2009, 69(16): 6539-6545).*
Tockman et al (Cancer Res., 1992, 52:2711s-2718s).*
(Continued)

*Primary Examiner* — Sean E Aeder
(74) *Attorney, Agent, or Firm* — Eversheds Sutherland (US) LLP

(57) ABSTRACT

Methods and biomarker panels for detecting and treating pancreatic disease, including pancreatic cancer, are provided in association with determining and inhibiting expression levels of certain GPCRs, including GPR68, in particular in pancreatic cancer associated fibroblasts.

8 Claims, 19 Drawing Sheets
Specification includes a Sequence Listing.

(56) References Cited

OTHER PUBLICATIONS

PCT International Search Report and Written Opinion for PCT Application No. PCT/US2018/053104 dated Jan. 15, 2019 (11 pages).
Chang, "Crosstalk Between Pancreatic Cancer Cells and Pancreatic Cancer-Associated Fibroblasts through Cytokines and a GPCR," University of California, San Diego, 2016, https://cloudfront.escolarship.org/dist/prd/content/q15p19p95rqt5p19p95r.pdf.

* cited by examiner

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccgttctta gttggtggag                                                     20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcacagacct gttattgctc aa                                                  22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccttccgctt ccaccagtt                                                      19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcgtcctcga tgacctcct                                                      19

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttactactgc tgagcgtgag at                                                  22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catgatgctg ttgtaggtgg tt                                                  22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcggaggaga gtcaggaagg                                                 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcaacaca gttacacaag ga                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acagccactc acctcttcag                                                 20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaagtctcc tcattgaatc ca                                              22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctggctact tctcgctct                                                  19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctctatccg cataggactg ac                                              22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acggtgcgat tcacatattc c                                              21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taatgtccag tctccaggtt gt                                             22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acattagtac acagcaccag aa                                             22

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctacaggca ggtcagtga                                                 19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggaatgaggt ggtcaacttc g                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatggagcg gatgtggtaa                                                20

GPCRS IN CANCER-ASSOCIATED FIBROBLASTS

CROSS REFERENCE TO RELATED APPLICATIONS

This application claims the priority benefit of PCT/US2018/053104 filed on Sep. 27, 2018 which claims the priority benefit of U.S. Provisional Application No. 62/563,884 filed Sep. 27, 2017, the entire contents of which are incorporated herein by reference.

STATEMENT OF GOVERNMENT INTEREST

The invention was made with government support under Grant No. CA121938 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Sep. 27, 2018, is named 24978-0462_SL.txt and is 4,323 bytes in size.

FIELD OF THE INVENTION

The invention relates to detection and treatment of cancers, and in particular, pancreatic cancer, facilitated by G protein-coupled receptor targeting.

BACKGROUND OF THE INVENTION

Pancreatic ductal adenocarcinoma (PDAC), the most common type of pancreatic cancer, is currently the third-leading cause of cancer death in the United States, and is predicted to be the second such cause by 2020 (1-3). The current 5-year survival rate of PDAC is ~8%. Factors that contribute to this high death rate include the early, asymptomatic phase of the disease, such that at the time of diagnosis, many patients have locally advanced or metastatic disease (1). Surgical resection, the only curative treatment, is feasible in <20% of patients. Chemotherapy of PDAC has had limited impact. The EGFR inhibitor erlotinib is the only approved targeted therapy and produces minimal clinical benefit (4, 5). Early detection, and new, effective treatments of pancreatic cancer are thus a major, unmet medical need.

Abundant fibrotic stroma (desmoplasia), a characteristic feature of PDAC, can comprise up to 80% of the tumor mass (6, 7). The dense stroma creates a hypovascular, hypoxic environment that contributes to drug resistance by inhibiting chemotherapeutic drug delivery to tumor cells (8, 9). Multiple cell types in the tumor microenvironment contribute to the regulation of the stroma in PDAC; these include pancreatic fibroblasts (PFs), pancreatic stellate cells (PSCs), vascular cells, and inflammatory/immune cells (9, 10). Activation of PFs and PSCs (by cytokines, growth factors, oxidative and metabolic stress) converts them into pancreatic cancer associated fibroblasts (CAFs), myofibroblastic cells that express abundant α-smooth muscle actin (α-SMA) and contribute to PDAC progression (11-13).

G protein-coupled receptors (GPCRs), the largest family of cell signaling receptors (~3% of the human genome), are seven transmembrane receptors that respond to numerous types of extracellular signals and regulate many physiological processes (14). GPCRs are the molecular entities most commonly targeted by FDA-approved drugs (15, 16). Emerging evidence implicates GPCRs in cancer: certain GPCRs have increased expression in tumors and are involved in cancer initiation and/or progression (17, 18). GPCRs can contribute to fibroblast-myofibroblast conversion (19) and increases in cellular cAMP (a second messenger for certain GPCRs) can blunt the myofibroblastic phenotype (20). Little is known regarding the role of GPCRs in CAFs.

SUMMARY OF THE INVENTION

The invention provides a method of detecting and/or treating a pancreatic disease in a patient comprising: obtaining a biological sample from the patient; detecting expression level of one or more GPCRs in the sample; determining that the expression level of the one or more GPCRs is greater than in a normal patient sample; and treating the patient for the pancreatic disease.

The invention also provides methods wherein the disease is cancer, wherein the expression level is detected by measuring RNA or protein, wherein the sample comprises pancreatic tissue or cells (including pancreatic cancer associated fibroblasts); wherein the treating inhibits the GPCR expression and/or activity; wherein the GPCR is GPR68; or wherein the GPCR is selected from a panel consisting of GPR68 along with other GPCRs that are highly expressed in pancreatic CAFs compared to CAF precursor cells (i.e., PFs and PSCs), including, OXTR, GPR56, GPRC5A, BDKRB1, PPYR1, GPR37, BDKRB2, ADRB2, F2RL1, EDG1, GPR51, FZD4, GPR150, and F2RL2.

The invention also provides a method wherein the GPCR is selected from a panel consisting of at least 5, 10, 15, 20, 25, 30, 35, 40, or 50 upregulated GPCRs as shown in the tables herein.

The invention also provides a biomarker panel for detecting pancreatic cancer comprising or consisting of at least 5, 10, 15, 20, 25, 30, 35, 40, or 50 upregulated GPCRs as shown in the tables herein.

The invention also provides a biomarker panel for detecting pancreatic cancer consisting of GPR68 and at least one other GPCR as shown in the tables herein.

DETAILED DESCRIPTION

Figure 1A:
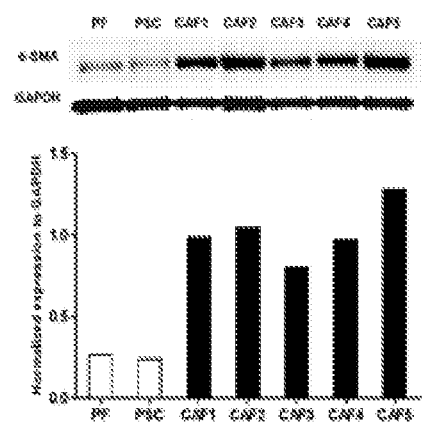
FIGS. 1A-1E show myofibroblastic phenotype and GPCR expression of pancreatic CAFs.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The invention provides a method of detecting and treating a pancreatic disease in a patient comprising: obtaining a biological sample from the patient; detecting expression level of one or more GPCRs in the sample; determining that the expression level of the one or more GPCRs is greater than in a normal or healthy control patient sample; and treating the patient for the pancreatic disease. A biologic sample may be a solid tissue biopsy or a fluid, such as blood or plasma.

The invention also provides methods wherein the disease is cancer; wherein the expression level is detected by measuring RNA or protein; wherein the sample comprises pancreatic tissue or cells (including pancreatic cancer associated fibroblasts), wherein the treating inhibits the GPCR expression and/or activity; wherein the GPCR is GPR68; or wherein the GPCR is selected from a panel consisting of GPR68 along with other GPCRs that are highly expressed in pancreatic CAFs compared to CAF precursor cells (i.e., PFs and PSCs), including, OXTR, GPR56, GPRC5A, BDKRB1, PPYR1, GPR37, BDKRB2, ADRB2, F2RL1, EDG1, GPR51, FZD4, GPR150, and F2RL2.

In embodiments, the invention is directed to detection of disease without treatment. The discovery of the role played by GPR68 and mechanisms for this role in pancreatic cancer are novel.

The invention also provides a method wherein the GPCR is selected from a panel consisting of at least 5, 10, 15, 20, 25, 30, 35, 40, or 50 upregulated GPCRs as shown in the tables herein.

The invention also provides a biomarker panel for detecting pancreatic cancer comprising or consisting of at least 5, 10, 15, 20, 25, 30, 35, 40, or 50 upregulated GPCRs as shown in the tables herein.

The invention also provides a biomarker panel for detecting pancreatic cancer consisting of GPR68 and at least one other upregulated GPCR as shown in the tables herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, 2nd ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20th ed., (Lippincott, Williams & Wilkins 2003), and Remington, The Science and Practice of Pharmacy, 22th ed., (Pharmaceutical Press and Philadelphia College of Pharmacy at University of the Sciences 2012).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutical acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition. In the case of treatment of pancreatic disease herein, conventional treatments such as surgical resection, chemotherapy, and radiology are contemplated, as well as the down regulation of overexpressed GPCRs, e.g., GPR68 such as by GPCR targeted antibodies, small molecule inhibitors, ph modification, and antisense nucleic acid therapy.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

The term "antibody" as used herein encompasses monoclonal antibodies (including full length monoclonal antibodies), polyclonal antibodies, multi-specific antibodies (e.g., bi-specific antibodies), and antibody fragments so long as they exhibit the desired biological activity of binding to a target antigenic site and its isoforms of interest. The term "antibody fragments" comprise a portion of a full length antibody, generally the antigen binding or variable region thereof. The term "antibody" as used herein encompasses any antibodies derived from any species and resources, including but not limited to, human antibody, rat antibody, mouse antibody, rabbit antibody, and so on, and can be synthetically made or naturally-occurring.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the monoclonal antibodies in humans, the monoclonal antibodies that have the desired function are preferably human or humanized. "Humanized" forms of non-human (e.g., murine) antibodies are chimeric antibodies that contain minimal sequence derived from non-human immunoglobulin. For the most part, humanized antibodies are human immunoglobulins (recipient antibody) in which hyper variable region residues of the recipient are replaced by hyper variable region residues from a non-human species (donor antibody) such as mouse, rat, rabbit or nonhuman primate having the desired specificity, affinity, and capacity. Furthermore, humanized antibodies may comprise residues that are not found in the recipient antibody or in the donor antibody. These modifications are made to further refine antibody performance.

The invention may also refer to any oligonucleotides (antisense oligonucleotide agents), polynucleotides (e.g. therapeutic DNA), ribozymes, DNA aptamers, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

"Amplification" refers to any known procedure for obtaining multiple copies of a target nucleic acid or its complement, or fragments thereof. The multiple copies may be referred to as amplicons or amplification products. Amplification, in the context of fragments, refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), reverse transcription polymerase chain reaction (RT-PCR), ligase chain reaction (LCR), strand-displacement amplification (SDA), and transcription-mediated or transcription-associated amplification. Amplification is not limited to the strict duplication of the starting molecule. For example, the generation of multiple cDNA molecules from RNA in a sample using reverse transcription (RT)-PCR is a form of amplification. Furthermore, the generation of multiple RNA molecules from a single DNA molecule during the process of transcription is also a form of amplification. During amplification, the amplified products can be labeled using, for example, labeled primers or by incorporating labeled nucleotides.

"Amplicon" or "amplification product" refers to the nucleic acid molecule generated during an amplification procedure that is complementary or homologous to a target nucleic acid or a region thereof. Amplicons can be double stranded or single stranded and can include DNA, RNA or both. Methods for generating amplicons are known to those skilled in the art.

"Codon" refers to a sequence of three nucleotides that together form a unit of genetic code in a nucleic acid.

"Codon of interest" refers to a specific codon in a target nucleic acid that has diagnostic or therapeutic significance (e.g. an allele associated with viral genotype/subtype or drug resistance).

"Complementary" or "complement thereof" means that a contiguous nucleic acid base sequence is capable of hybridizing to another base sequence by standard base pairing (hydrogen bonding) between a series of complementary bases. Complementary sequences may be completely complementary (i.e. no mismatches in the nucleic acid duplex) at each position in an oligomer sequence relative to its target sequence by using standard base pairing (e.g., G:C, A:T or A:U pairing) or sequences may contain one or more positions that are not complementary by base pairing (e.g., there exists at least one mismatch or unmatched base in the nucleic acid duplex), but such sequences are sufficiently complementary because the entire oligomer sequence is capable of specifically hybridizing with its target sequence in appropriate hybridization conditions (i.e. partially complementary). Contiguous bases in an oligomer are typically at least 80%, preferably at least 90%, and more preferably completely complementary to the intended target sequence.

"Configured to" or "designed to" denotes an actual arrangement of a nucleic acid sequence configuration of a referenced oligonucleotide. For example, a primer that is configured to generate a specified amplicon from a target nucleic acid has a nucleic acid sequence that hybridizes to the target nucleic acid or a region thereof and can be used in an amplification reaction to generate the amplicon. Also as an example, an oligonucleotide that is configured to specifically hybridize to a target nucleic acid or a region thereof has a nucleic acid sequence that specifically hybridizes to the referenced sequence under stringent hybridization conditions.

"Downstream" means further along a nucleic acid sequence in the direction of sequence transcription or read out.

"Upstream" means further along a nucleic acid sequence in the direction opposite to the direction of sequence transcription or read out.

"Polymerase chain reaction" (PCR) generally refers to a process that uses multiple cycles of nucleic acid denaturation, annealing of primer pairs to opposite strands (forward and reverse), and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. There are many permutations of PCR known to those of ordinary skill in the art.

"Position" refers to a particular amino acid or amino acids in a nucleic acid sequence.

"Primer" refers to an enzymatically extendable oligonucleotide, generally with a defined sequence that is designed to hybridize in an antiparallel manner with a complementary, primer-specific portion of a target nucleic acid. A primer can initiate the polymerization of nucleotides in a template-dependent manner to yield a nucleic acid that is complementary to the target nucleic acid when placed under suitable nucleic acid synthesis conditions (e.g. a primer annealed to a target can be extended in the presence of nucleotides and a DNA/RNA polymerase at a suitable temperature and pH). Suitable reaction conditions and reagents are known to those of ordinary skill in the art. A primer is typically single stranded for maximum efficiency in amplification, but may alternatively be double stranded. If double stranded, the primer is generally first treated to separate its strands before being used to prepare extension products. The primer generally is sufficiently long to prime the synthesis of extension products in the presence of the inducing agent (e.g. polymerase). Specific length and sequence will be dependent on the complexity of the required DNA or RNA targets, as well as on the conditions of primer use such as temperature and ionic strength. Preferably, the primer is about 5-100 nucleotides. Thus, a primer can be, e.g., 5, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95 or 100 nucleotides in length. A primer does not need to have 100% complementarity with its template for primer elongation to occur; primers with less than 100% complementarity can be sufficient for hybridization and polymerase elongation to occur. A primer can be labeled if desired. The label used on a primer can be any suitable label, and can be detected by, for example, spectroscopic, photochemical, biochemical, immunochemical, chemical, or other detection means. A labeled primer therefore refers to an oligomer that hybridizes specifically to a target sequence in a nucleic acid, or in an amplified nucleic acid, under conditions that promote hybridization to allow selective detection of the target sequence.

A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. One of skill in the art will recognize that, in certain embodiments, primer nucleic acids can also be used as probe nucleic acids.

"Region" refers to a portion of a nucleic acid wherein said portion is smaller than the entire nucleic acid.

"Region of interest" refers to a specific sequence of a target nucleic acid that includes all codon positions having at least one single nucleotide substitution mutation associated with a genotype and/or subtype that are to be amplified and detected, and all marker positions that are to be amplified and detected, if any.

"RNA-dependent DNA polymerase" or "reverse transcriptase" ("RT") refers to an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

"DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

"DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

A "sequence" of a nucleic acid refers to the order and identity of nucleotides in the nucleic acid. A sequence is typically read in the 5' to 3' direction. The terms "identical" or percent "identity" in the context of two or more nucleic acid or polypeptide sequences, refer to two or more sequences or subsequences that are the same or have a specified percentage of amino acid residues or nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" J. Mol. Biol. 215:403-410, Gish et al. (1993) "Identification of protein coding regions by database similarity search" Nature Genet. 3:266-272, Madden et al. (1996) "Applications of network BLAST server" Meth. Enzymol. 266:131-141, Altschul et al. (1997) "Gapped BLAST and PSI-BLAST: a new generation of protein database search programs" Nucleic Acids Res. 25:3389-3402, and Zhang et al. (1997) "PowerBLAST: A new network BLAST application for interactive or automated sequence analysis and annotation" Genome Res. 7:649-656, which are each incorporated by reference. Many other optimal alignment algorithms are also known in the art and are optionally utilized to determine percent sequence identity.

A "label" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), weakly fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

A "linker" refers to a chemical moiety that covalently or non-covalently attaches a compound or substituent group to another moiety, e.g., a nucleic acid, an oligonucleotide probe, a primer nucleic acid, an amplicon, a solid support, or the like. For example, linkers are optionally used to attach oligonucleotide probes to a solid support (e.g., in a linear or other logic probe array). To further illustrate, a linker optionally attaches a label (e.g., a fluorescent dye, a radioisotope, etc.) to an oligonucleotide probe, a primer nucleic acid, or the like. Linkers are typically at least bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Exemplary linkers include, e.g., oligopeptides, oligonucleotides, oligopolyamides, oligoethyleneglycerols, oligoacrylamides, alkyl chains, or the like. Additional description of linker molecules is provided in, e.g., Hermanson, Bioconjugate Techniques, Elsevier Science (1996), Lyttle et al. (1996) Nucleic Acids Res. 24(14):2793, Shchepino et al. (2001) Nucleosides, Nucleotides, & Nucleic Acids 20:369, Doronina et al (2001) Nucleosides, Nucleotides, & Nucleic Acids 20:1007, Trawick et al. (2001) Bioconjugate Chem. 12:900, Olejnik et al. (1998) Methods in Enzymology 291:135, and Pljevaljcic et al. (2003) J. Am. Chem. Soc. 125(12):3486, all of which are incorporated by reference.

"Fragment" refers to a piece of contiguous nucleic acid that contains fewer nucleotides than the complete nucleic acid.

"Hybridization," "annealing," "selectively bind," or "selective binding" refers to the base-pairing interaction of one nucleic acid with another nucleic acid (typically an antiparallel nucleic acid) that results in formation of a duplex or other higher-ordered structure (i.e. a hybridization complex). The primary interaction between the antiparallel nucleic acid molecules is typically base specific, e.g., A/T and G/C. It is not a requirement that two nucleic acids have 100% complementarity over their full length to achieve hybridization. Nucleic acids hybridize due to a variety of well characterized physio-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, New York), as well as in Ausubel (Ed.) Current Protocols in Molecular Biology, Volumes I, II, and III, 1997, which is incorporated by reference.

The term "attached" or "conjugated" refers to interactions and/or states in which material or compounds are connected or otherwise joined with one another. These interactions and/or states are typically produced by, e.g., covalent bonding, ionic bonding, chemisorption, physisorption, and combinations thereof.

A "composition" refers to a combination of two or more different components. In certain embodiments, for example, a composition includes one or more oligonucleotide probes in solution.

The term "derivative" refers to a chemical substance related structurally to another substance, or a chemical substance that can be made from another substance (i.e., the substance it is derived from), e.g., through chemical or enzymatic modification. To illustrate, oligonucleotide probes are optionally conjugated with biotin or a biotin derivative. To further illustrate, one nucleic acid can be "derived" from another through processes, such as chemical synthesis based on knowledge of the sequence of the other nucleic acid, amplification of the other nucleic acid, or the like.

"Nucleic acid" or "nucleic acid molecule" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid backbone can be made up of a variety of linkages, including one or more of sugar-phosphodiester linkages, peptide-nucleic acid bonds, phosphorothioate linkages, methylphosphonate linkages, or combinations thereof. Sugar moieties of the nucleic acid can be ribose, deoxyribose, or similar compounds having known substitutions (e.g. 2'-methoxy substitutions and 2'-halide substitutions). Nitrogenous bases can be conventional bases (A, G, C, T, U) or analogs thereof (e.g., inosine, 5-methylisocytosine, isoguanine). A nucleic acid can comprise only conventional sugars, bases, and linkages as found in RNA and DNA, or can include conventional components and substitutions (e.g., conventional bases linked by a 2'-methoxy backbone, or a nucleic acid including a mixture of conventional bases and one or more base analogs). Nucleic acids can include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA). Nucleic acids can include modified bases to alter the function or behavior of the nucleic acid (e.g., addition of a 3'-terminal dideoxynucleotide to block additional nucleotides from being added to the nucleic acid). Synthetic methods for making nucleic acids in vitro are well known in the art although nucleic acids can be purified from natural sources using routine techniques. Nucleic acids can be single-stranded or double-stranded.

A nucleic acid is typically single-stranded or double-stranded and will generally contain phosphodiester bonds, although in some cases, as outlined, herein, nucleic acid analogs are included that may have alternate backbones, including, for example and without limitation, phosphoramide (Beaucage et al. (1993) Tetrahedron 49(10):1925 and references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110: 4470; and Pauwels et al. (1986) Chemica Scripta 26: 1419, which are each incorporated by reference), phosphorothioate (Mag et al. (1991) Nucleic Acids Res. 19:1437; and U.S. Pat. No. 5,644,048, which are both incorporated by reference), phosphorodithioate (Briu et al. (1989) J. Am. Chem. Soc. 111:2321, which is incorporated by reference), O-methylphosphoroamidite linkages (see Eckstein, Oligonucleotides and Analogues: A Practical Approach, Oxford University Press (1992), which is incorporated by reference), and peptide nucleic acid backbones and linkages (see, Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207, which are each incorporated by reference). Other analog nucleic acids include those with positively charged backbones (Denpcy et al. (1995) Proc. Natl. Acad. Sci. USA 92:6097, which is incorporated by reference); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem: Lett. 4: 395; Jeffs et al. (1994) J. Biomolecular NMR 34:17; and Tetrahedron Lett. 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (TO modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

An "oligonucleotide" or "oligomer" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; or the solid support method of U.S. Pat. No. 4,458,066, or other methods known in the art. All of these references are incorporated by reference.

A "mixture" refers to a combination of two or more different components. A "reaction mixture" refers a mixture that comprises molecules that can participate in and/or facilitate a given reaction. An "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components, which includes the modified primers of the invention.

The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent agent or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of an agent or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. An agent or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

The term "pharmaceutically acceptable carrier" as used herein refers to an excipient, diluent, preservative, solubilizer, emulsifier, adjuvant, and/or vehicle with which an agent or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Other embodiments and uses are apparent to one skilled in the art in light of the present disclosures. Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

EXAMPLES

GPCRs Expressed by Pancreatic CAFs, PFs and PSCs

Pancreatic CAF cultures, which express substantial α-SMA, were generated from primary tumors of five PDAC patients (FIG. 1A). RNA-seq analysis confirmed that compared to PSCs (CAF precursor cells), CAFs have higher expression of numerous pro-fibrotic genes, including matrix and stress fiber proteins, cytokines and growth factors (FIG. 1B) (12).

Of the >800 GPCRs in the human genome, ~350 are non-chemosensory (other than visual, odorant, or tastant) (26) receptors. We quantified GPCRs expressed in the five CAF samples by using Taqman GPCR arrays, which assess the expression of 341 non-chemosensory GPCRs. We used 18S rRNA as a reference gene and a ΔCt value ≤25 as the threshold for detection of GPCRs. The five CAF samples expressed 105, 100, 112, 116, 117 GPCRs, respectively (FIG. 1C), of which 82 GPCRs (including 31 orphan GPCRs) were shared among the five samples. Table 2 lists the CAF-expressed GPCRs.

PFs and PSCs expressed 84 and 100 GPCRs, respectively. Of the 82 commonly detected GPCRs in CAFs, expression of 39 and 37 was >2-fold greater than in PSCs and PFs, respectively; 25 of those GPCRs were increased in CAFs compared to both PFs and PSCs. Few GPCRs had >50% decreased expression in CAFs; adenosine A2b (ADORA2B) was the only GPCR with consistently decreased expression in CAFs. Of note, 9 and 16 GPCRs were uniquely expressed by CAFs but not in PSCs or PFs, respectively (FIG. 1D, Table 3, and Table 4).

Figure 1B:
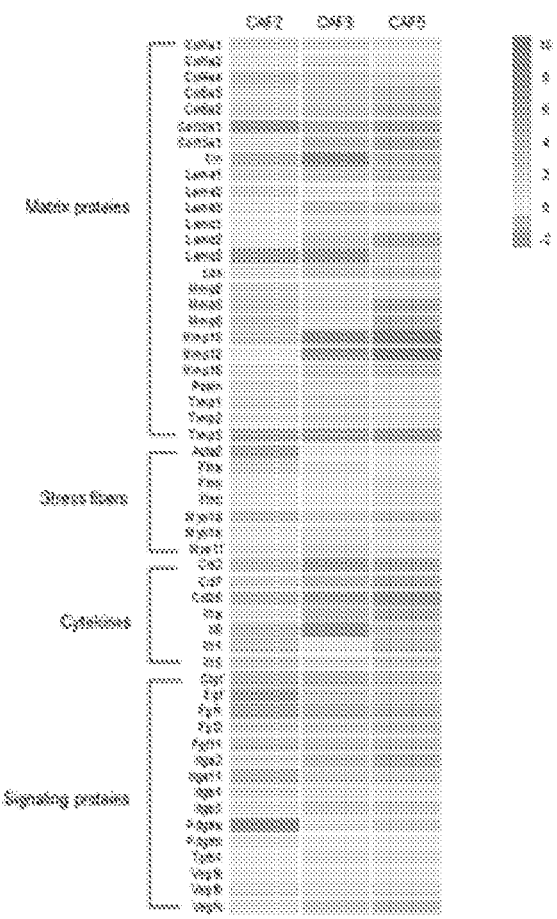
Figure 1C:
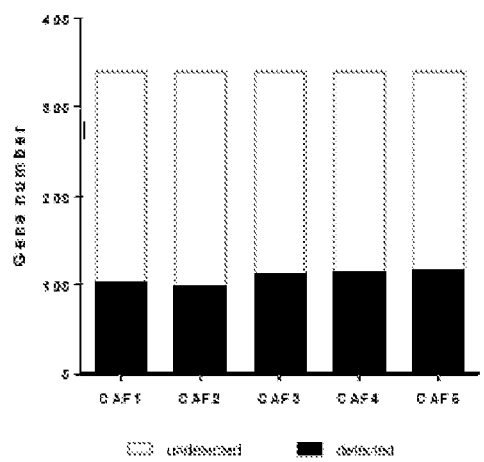
Figure 1D:
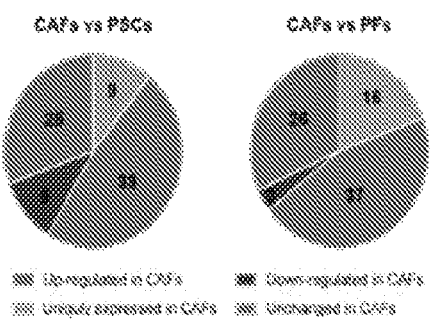
Figure 1E:
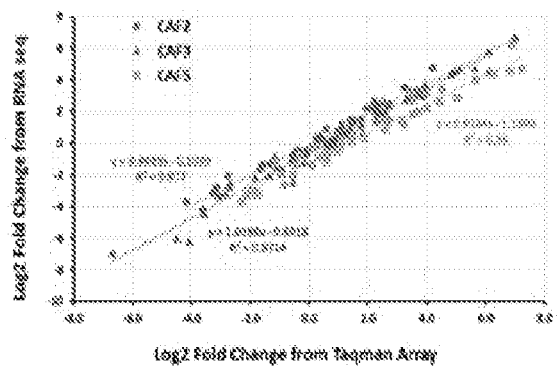

Log 2-fold changes from the Taqman GPCR array data correlated closely with RNA-seq data for three CAF cell lines, CAF2, CAF3 and CAF5 (R2>0.96 for all 3), providing validation for the use of Taqman GPCR arrays as a means to assess GPCR expression (FIG. 1E). A heat map of the Log 2-fold change of GPCRs in CAFs compared to PSCs showed similar patterns between GPCR array and RNA-seq data (Table 2). Four GPCRs, G protein-coupled receptor 56 (GPR56), G protein-coupled receptor 68 (GPR68), somatostatin receptor 1 (SSTR1) and G protein-coupled receptor class C group 5 member A (GPRC5A), were among the 10 most highly up-regulated GPCRs in CAFs compared to both PSCs and PFs (Table 1). The ΔCt values of GPR56, GPR68, SSTR1 and GPRC5A in CAFs (18.7, 17.5, 17.2 and 15.2, respectively) indicated that they are also relatively highly expressed in CAFs.

Figure 2A:
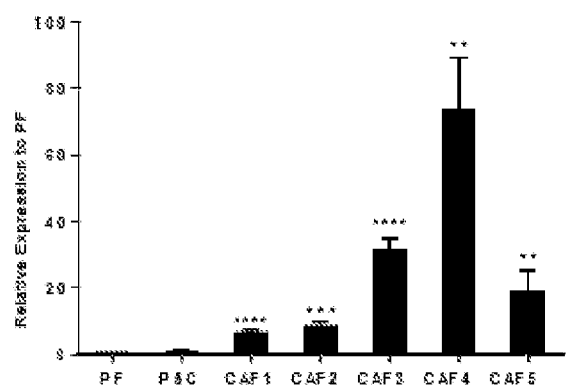
FIGS. 2A-2E show increased GPR68 mRNA and protein expression in pancreatic CAFs and PDAC tumors.
Figure 2B:
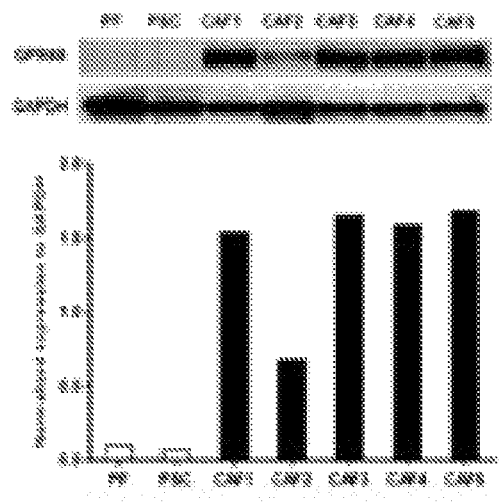
Figure 8:
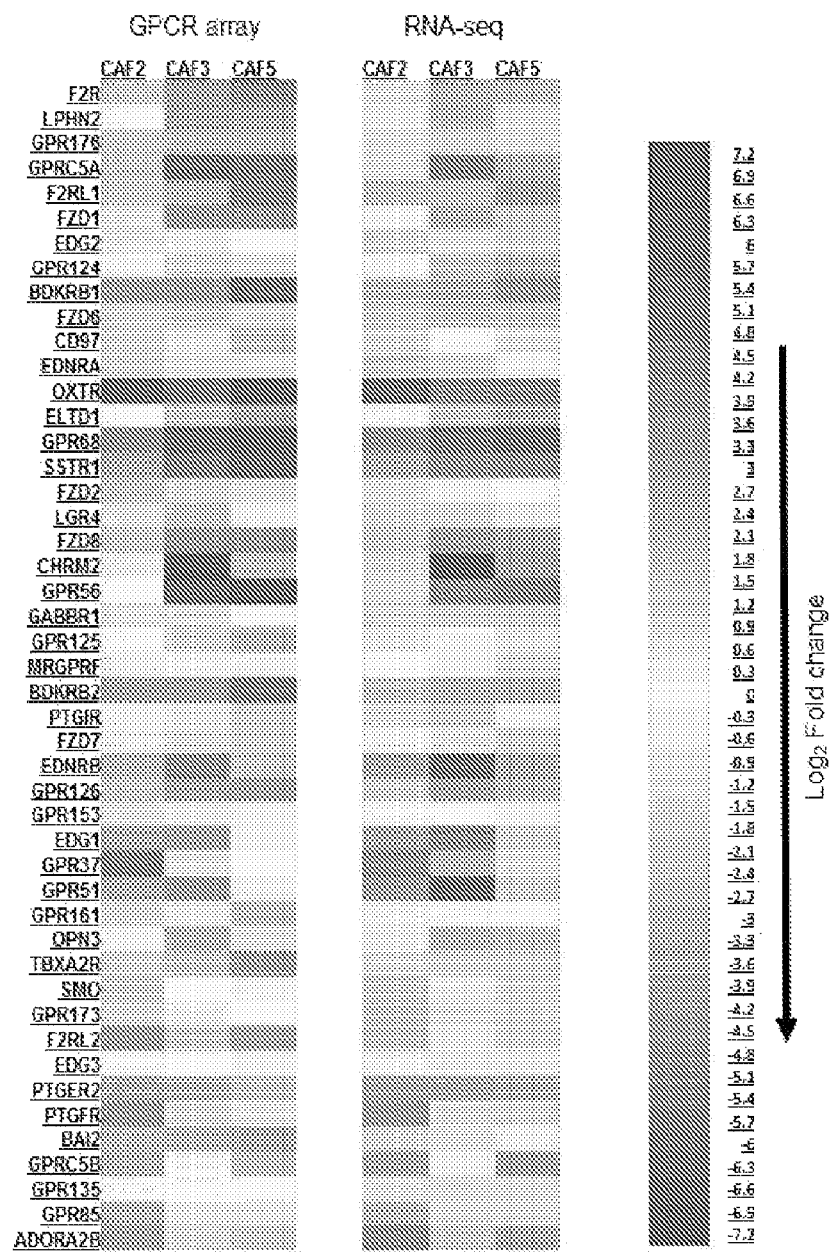
FIG. 8 shows a heat map of the log 2 of fold-changes of GPCRs expressed by each of 3 CAF samples compared to PSCs, as assayed using GPCR arrays and RNA-seq. GPCR expression by CAFs is listed from the highest (top) to lowest expressed (bottom). GPCRs not detected in PSCs (i.e., ΔCt>25) were excluded from this plot.

GPR68 is up-regulated in CAFs compared to PFs and PSCs and its fold-increase in PDAC compared to normal pancreas is greater than for other cancers relative to their normal precursor tissues Taqman GPCR array data revealed that GPR68 is the 2nd most highly up-regulated GPCR in CAFs compared to both PSCs and PFs (Table 1). GPR68 belongs to a family of proton-sensing GPCRs along with GPR4, GPR65, and GPR132 (27). GPR68 was the focus of interest because of the acidic microenvironment in PDAC tumors and because GPR68 has been implicated as a tumor suppressor or promoter in other types of cancer (28). Real-time qPCR confirmed that GPR68 expression is increased 7-70 fold in pancreatic CAFs compared to PSCs and PFs (FIG. 2A). RNA-seq data in another study (12) also revealed higher GPR68 expression in pancreatic CAFs/activated PSCs (Table 3). Compared to PSCs and PFs, CAFs have increased GPR68 protein expression (FIG. 2B). PDAC patient tumors (32 of 38 tumors, 84%) showed high GPR68 expression in the tumor stroma (FIG. 2C); most PDAC tumors without increased GPR68 had medullary invasion by PDAC cells and lacked CAFs (Table 4). Other proton-sensing GPCRs are not expressed by CAFs (Table 5). Analysis of publicly available RNA-seq data showed that on average, GPR68 expression is 10.5-fold higher in 147 PDAC tumors than 165 normal pancreases (FIG. 2D). PDAC has the highest fold-increase in GPR68 expression compared to normal tissue among 45 types of cancer (FIG. 2E). GPR68 is also the only proton-sensing GPCR detected in all three PDAC cell lines, AsPC-1, BxPC-3 and MIA PaCa-2 (FIG. 8).

Figure 3A:
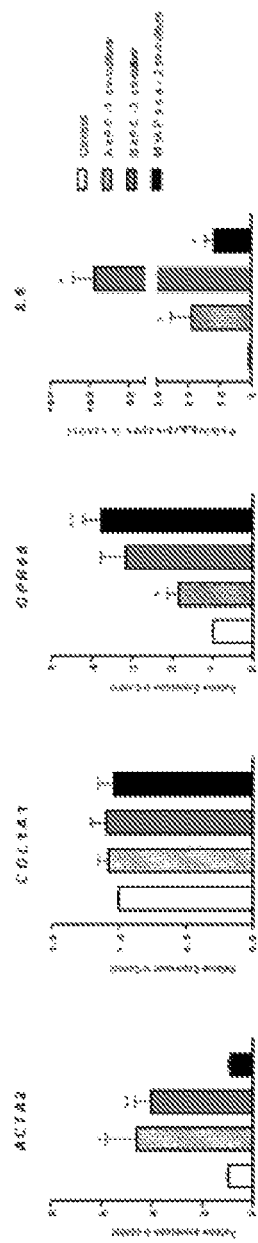
FIGS. 3A-3D show co-culture of PDAC cells and PSCs increases expression by PSCs of GPR68 and fibrotic genes, effects mediated by TNFα and TGFβ, respectively.
Figure 3B:
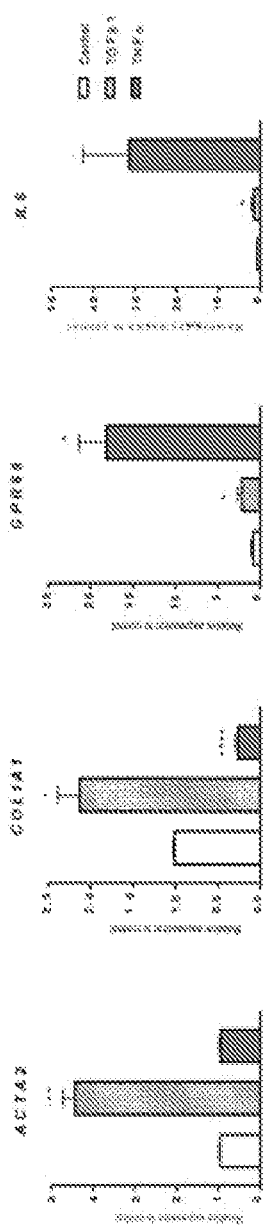
Figure 3C:
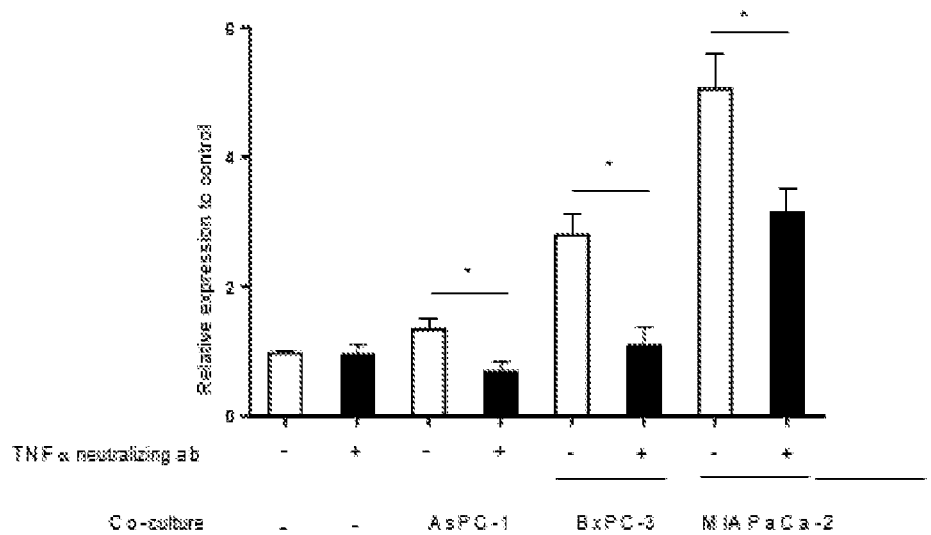
Figure 3D:
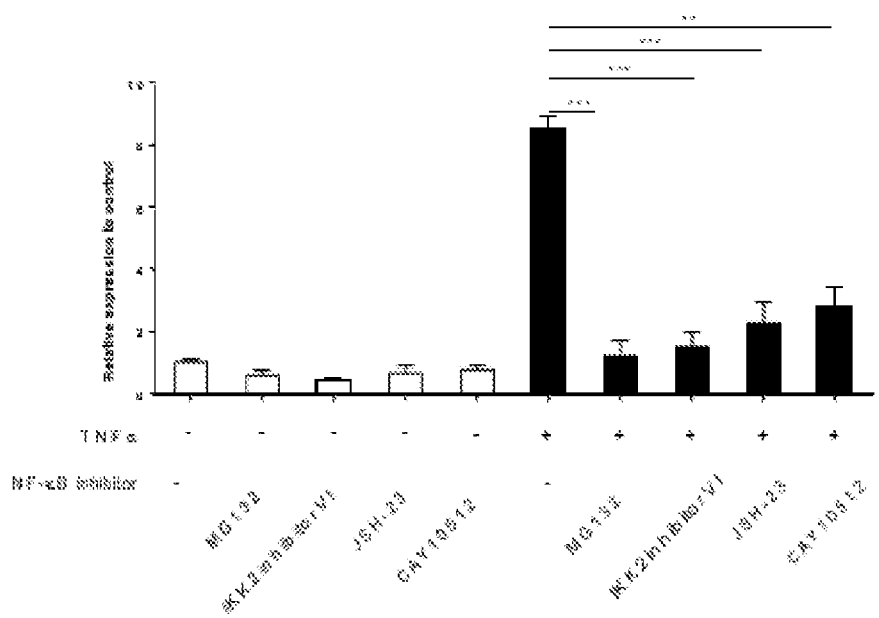
Figure 4A:
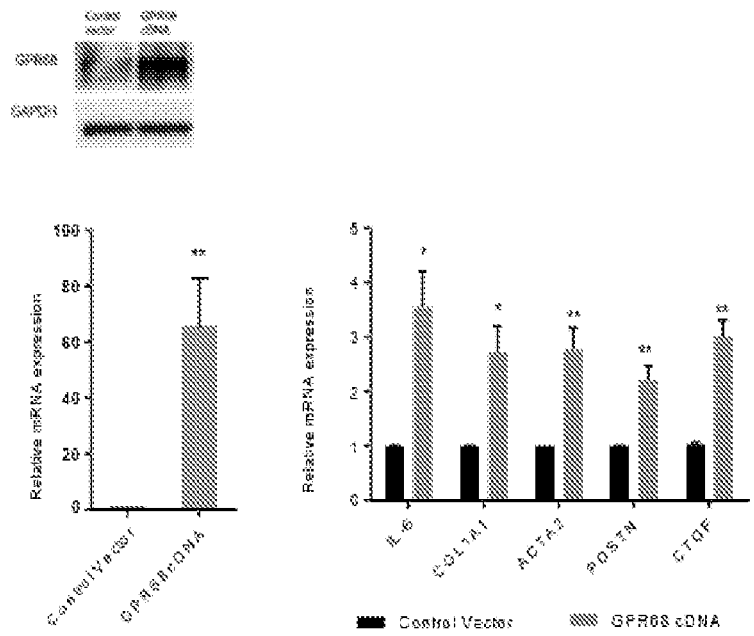
FIGS. 4A-4D show gain-of-function of GPR68 in PSCs and loss-of-function studies of GPR68 in pancreatic CAFs.
Figure 4B:
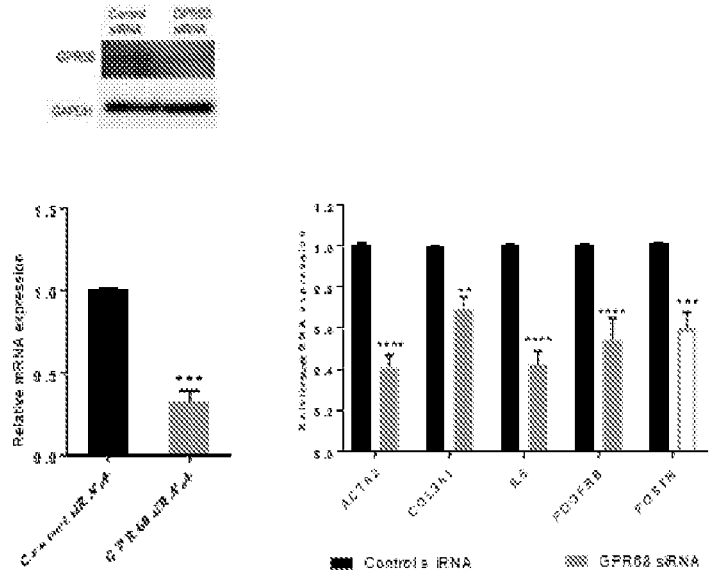
Figure 4C:
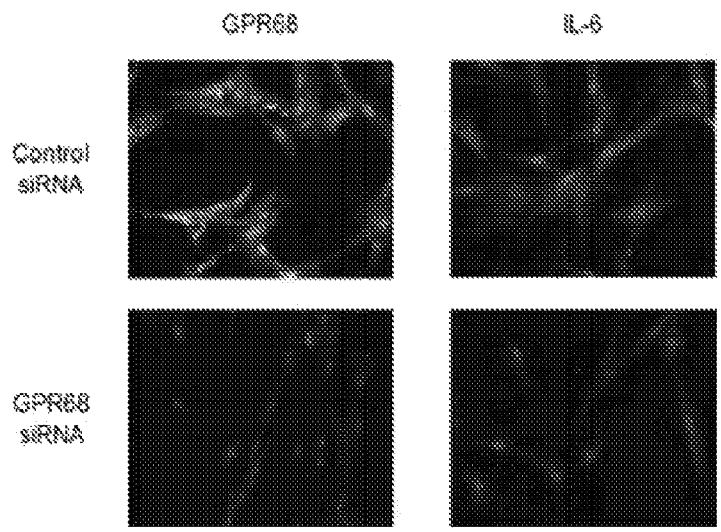
Figure 9:
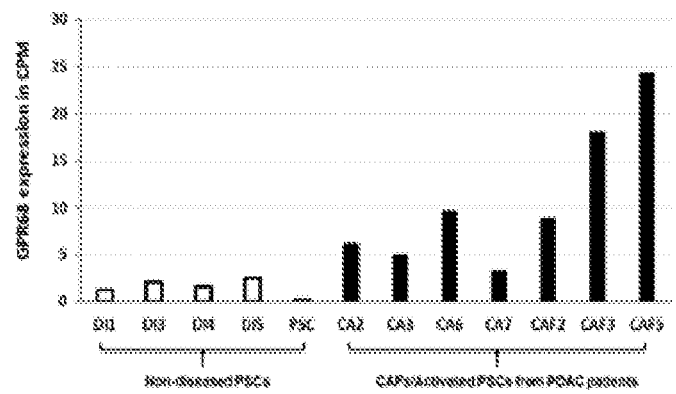
FIG. 9 shows a public RNA-seq data mined for analysis of GPR68 expression
Figures 10A, 10B, 10C, 10D, 10E, 10F:
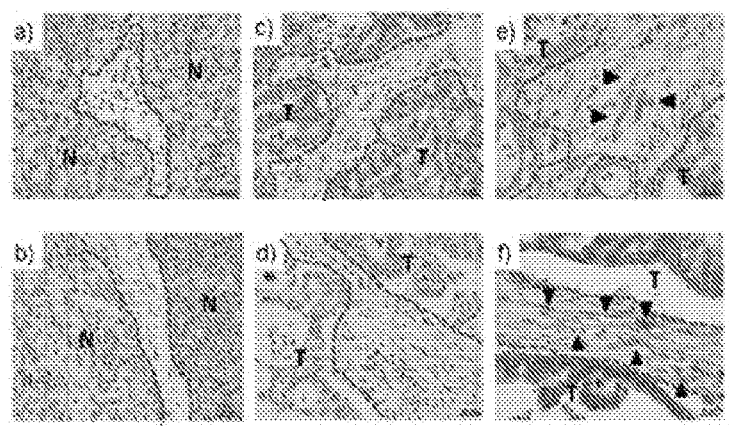
FIGS. 10A-10F show immunohistochemistry of GPR68 in normal pancreatic tissues and in pancreas with PDAC.
Figures 16A, 16B, 16C:
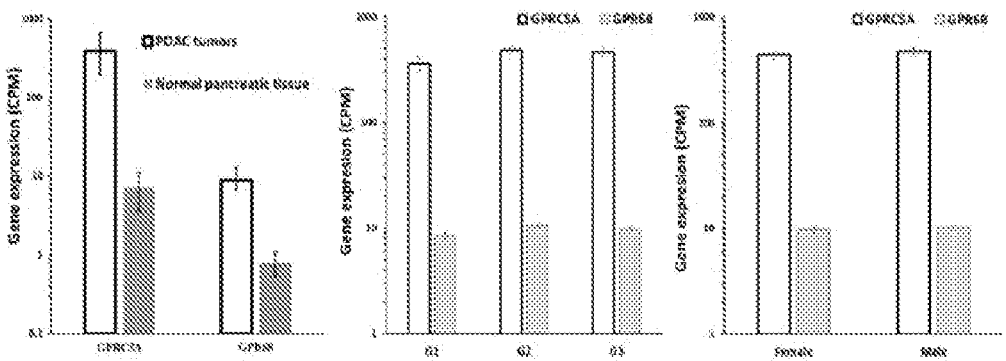
FIGS. 16A-16C show that GPRC5A and GPR68 are highly expressed in PDAC tumors and expression of each GPCR in tumors that are grades G1, G2 and G3 and in women and men.

Analysis of differential gene expression in PDAC tumors (TCGA) compared to normal pancreatic tissue (GTEx) revealed that GPRC5A and GPR68 are more highly expressed in the tumors than in normal tissue: GPRC5A is ~50-fold increased in PDAC and GPR68 has ~10-fold increased expression, each with a False Discovery Rate (FDR)<<0.05, indicating high statistical significance (FIG. 16A). Both GPCRs shown no evidence for dependence on tumor grade or a patient's sex (FIGS. 16B and 16C), suggesting, respectively, that expression of GPR68 and GPRC5A increases early in tumor development and is highly prevalent in both male and female PDAC patients.
TNFα Increases GPR68 Expression in PSCs PDAC cells and PSCs have bidirectional crosstalk (29, 30). PDAC cells can activate PSCs and increase their proliferation and migration; Transforming growth factor beta 1 (TGFβ1) is a "driver" of PSC activation (31, 32). A transwell co-culture system was used to study interaction between PDACs and PSCs. Co-culture of PSCs with AsPC-1, BxPC-3 or MIA PaCa-2 cells increased the expression of GPR68, α-SMA (ACTA2) and IL-6 (FIG. 3A). Incubation of PSCs with TGFβ1 increased expression of ACTA2 and COL1A1 but did not change GPR68 expression (FIG. 3B). By contrast, PSCs incubated with tumor necrosis factor-α (TNFα) another factor that can alter fibroblast function, had 18-fold higher expression of GPR68 and 31-fold higher expression of IL-6, but not higher ACTA2 or COL1A1 expression (FIG. 3B). These results suggest that regulation of GPR68 expression in PSCs depends on TNFα but is independent of TGFβ-promoted transformation of PSCs to myofibroblasts. Indeed, adding TNFα neutralizing antibody to the co-culture system diminished the PDAC-induced increase in GPR68 expression in PSCs (FIG. 3C). Furthermore, four NF-κB inhibitors, MG132, IKK2 inhibitor VI, JSH-23 and CAY10512, reduced the TNFα-promoted increase in GPR68 expression in PSCs (FIG. 3D). Together, the results imply that PDAC cells release TNFα, which acts via NF-κB in PSCs to increase GPR68 expression, a pathway for GPR68 induction akin to that of mono-mac 6 cells (33). To test if hypoxia up-regulates GPR68 expression (34), we cultured PSCs in 1% O2 for 48 h and found a 1.7-fold increase in GPR68 expression compared to that of normoxia-cultured PSCs but hypoxia did not significantly change the expression of fibrotic (myofibroblast) markers in the PSCs (FIG. 9).
GPR68 Regulates IL-6 Production in CAFs Gain-of-function and loss-of-function approaches was used to assess GPR68 function. Transfection of PSCs with GPR68 cDNA increased expression of myofibroblast markers: ACTA2, COL1A1, IL-6, POSTN and CTGF (FIG. 4A). Knockdown of GPR68 in CAFs with siRNA decreased expression of ACTA2, COL3A1, IL-6, POSTN and PDG-FRB (FIG. 4B). IL-6 protein was reduced in CAFs with GPR68 knockdown (FIG. 4C). The effect of GPR68 on cell viability was tested in conditions that mimic the in vivo acidic tumor microenvironment (35, 36). After 48 h incubation, viability of CAFs at pH 6.6 and 6.4 was reduced compared to that at pH 7.4; CAFs with GPR68 knockdown had even less viability (FIG. 4D), suggesting that GPR68 may help maintain CAF viability in acidic conditions. GPR68 knockdown did not alter CAF viability at pH's 7.4, 7.2, 7.0 or 6.8 (FIG. 4D) or affect growth of CAFs (for 96 h) at pH 7.4 or 6.8 (FIGS. 10A-10F).

Figure 5A:
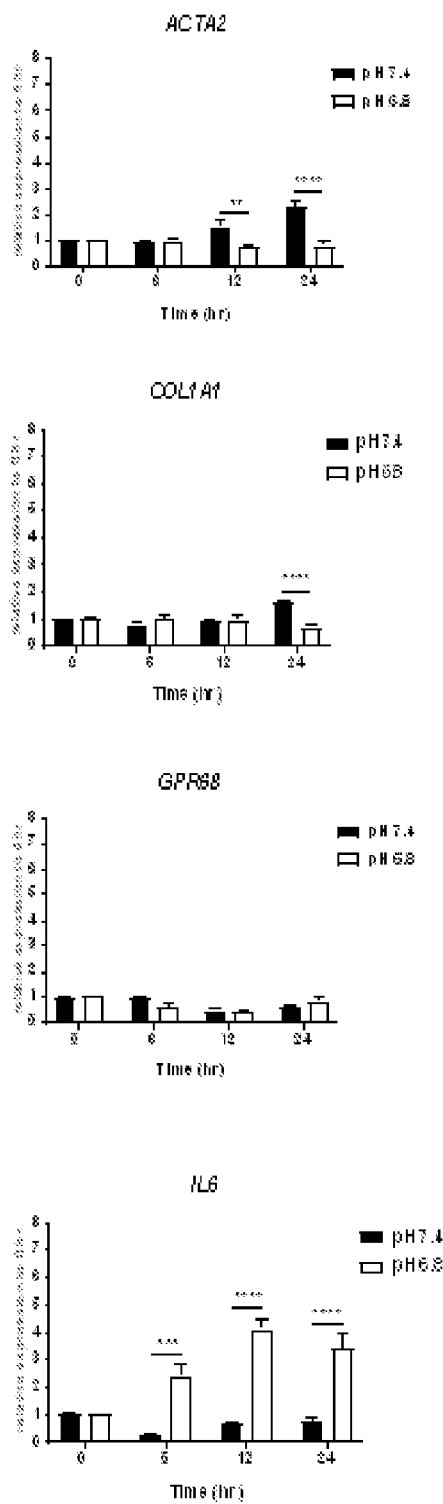
FIGS. 5A-5D shows the effect of growth at low pH and of GPR68 on gene expression and IL-6 expression by CAFs and PDAC cell proliferation.
Figure 5B:
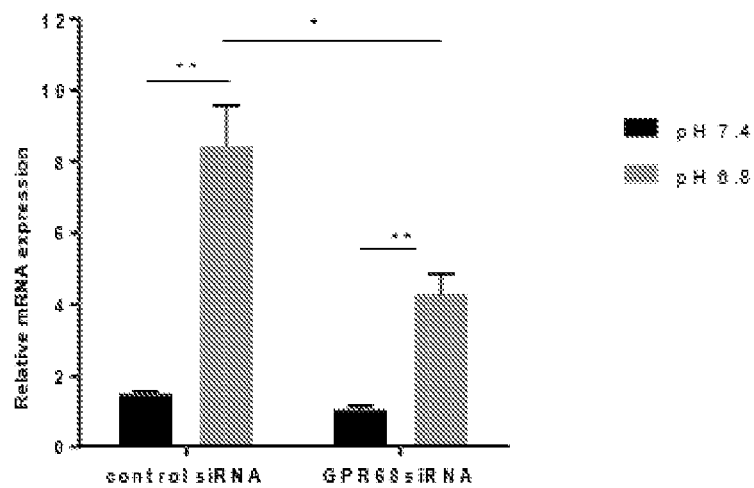
Figure 5C:
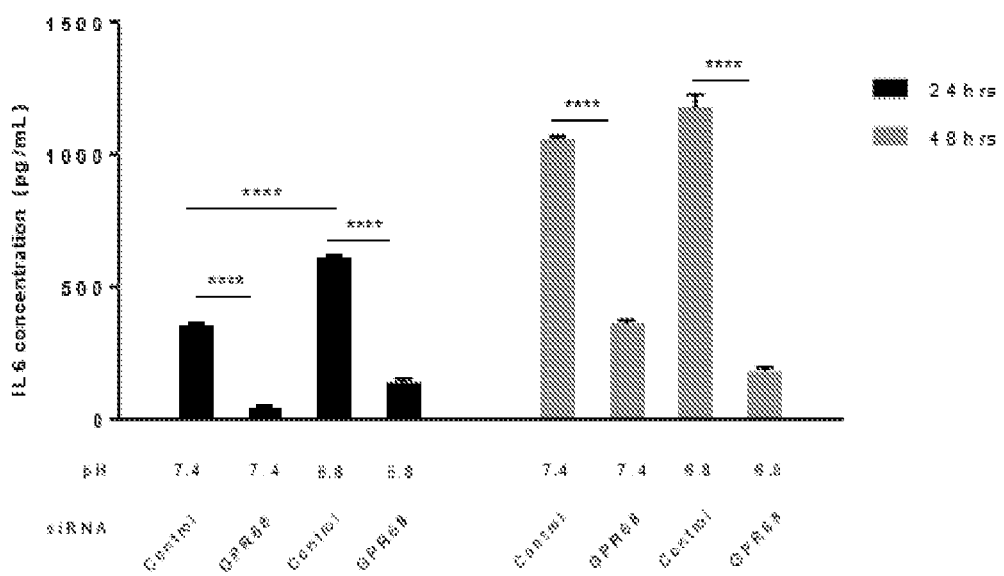
Figure 5D:
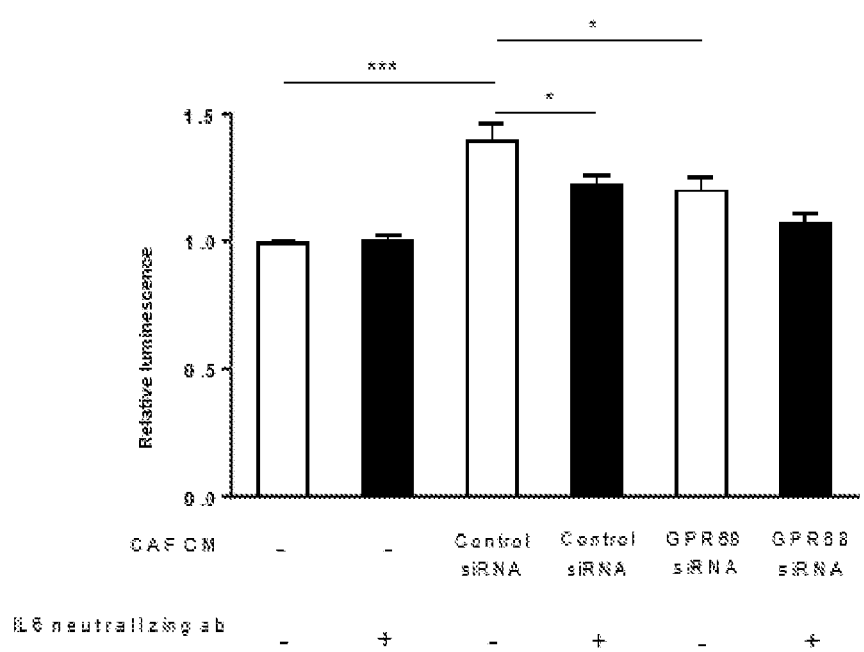
Figure 6A:
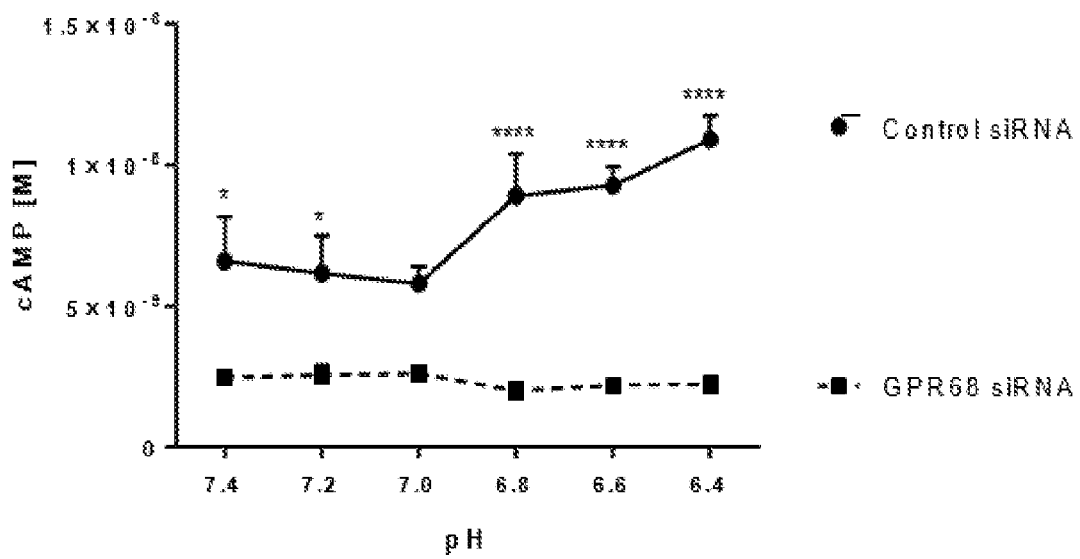
FIGS. 6A-6D shows pH-dependent activation of GPR68, which acts via cAMP/PKA/CREB to increase IL6 production by pancreatic CAFs.
Figure 6B:
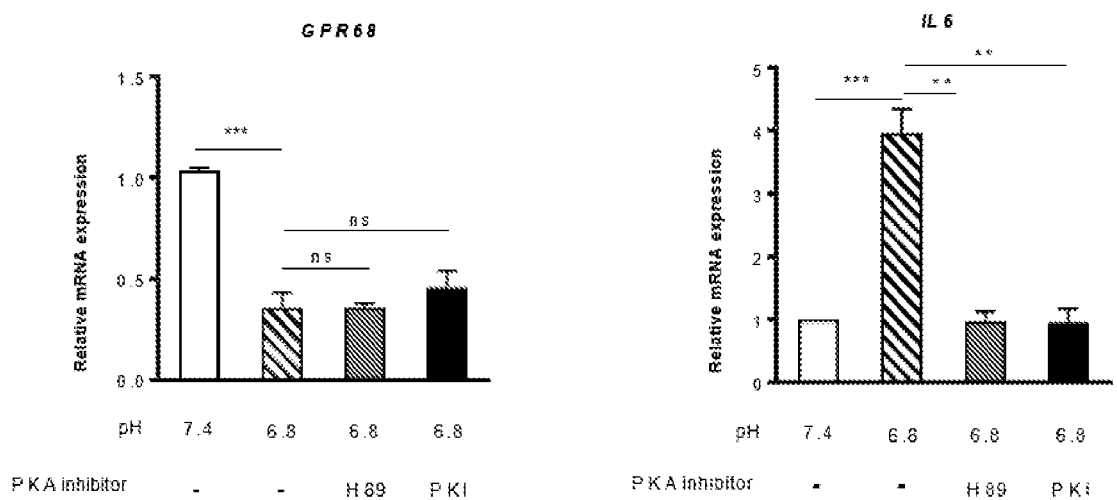
Figure 6C:
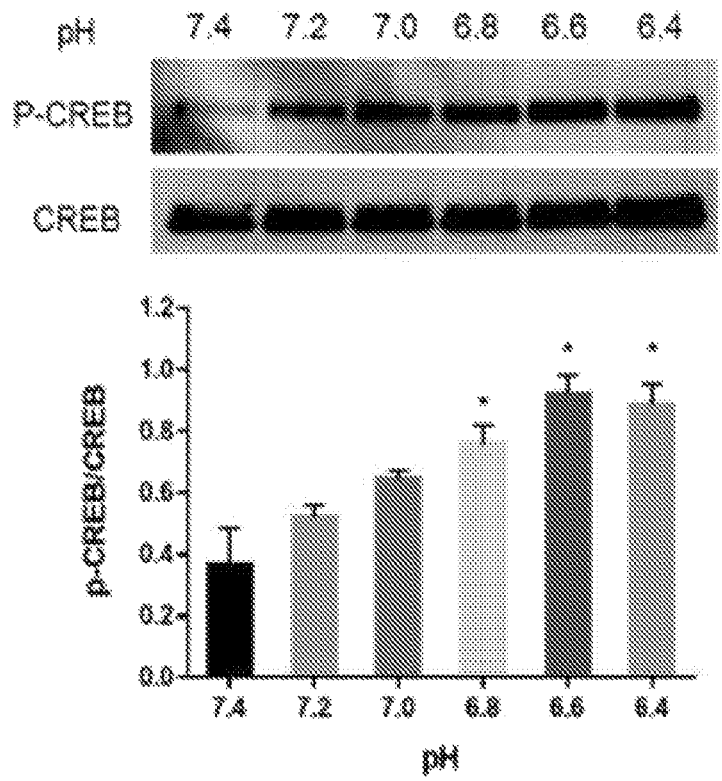
Figure 6D:
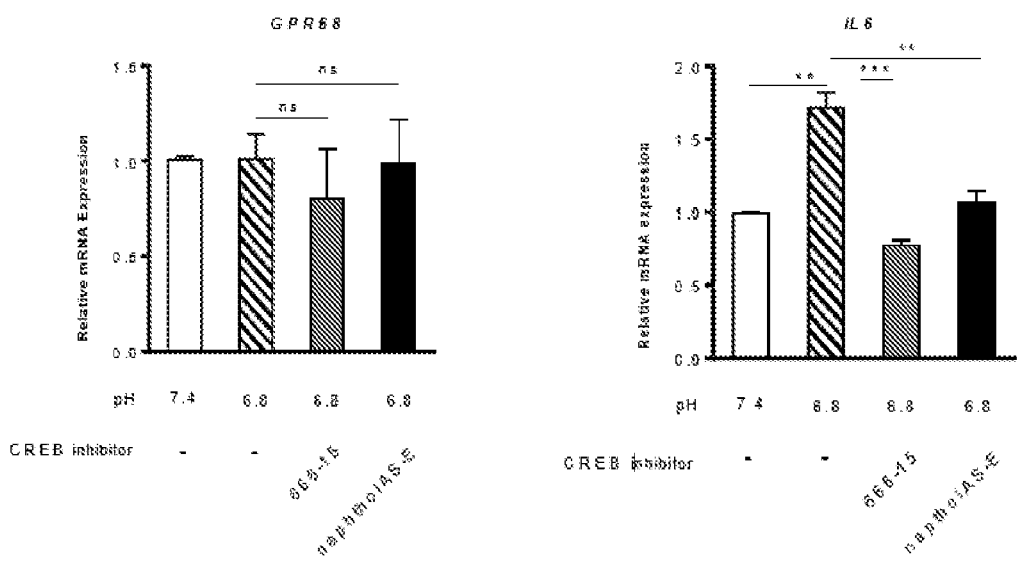

To further investigate the role of GPR68 in gene regulation, incubated CAFs were circulated at pH 7.4 and pH 6.8 (a pH that activates GPR68 (27)). At pH 6.8, expression of IL-6 was increased, of ACTA1 and COL1A1 was lower while that of GPR68 was unchanged (FIG. 5A). GPR68 knockdown in CAFs diminished the pH 6.8-induced increase in IL-6 mRNA expression (FIG. 5B). GPR68 knockdown also decreased IL-6 protein present in conditioned media (CM) of CAFs cultured at both pH 7.4 and pH 6.8 (FIG. 5C). Addition of CAF CM enhanced PDAC (BxPC-3) cell proliferation, a response that was reduced in CM treated with IL-6 neutralizing antibody or from CAFs with GPR68 knockdown (FIG. 5D). Activation of GPR68 by extracellular protons thus enhances IL-6 expression in CAFs and the resultant increase in IL-6 in CAF CM can stimulate PDAC cell proliferation.
GPR68 Regulates IL-6 Production Through cAMP-PKA-CREB in CAFs GPR68 can couple to heterotrimeric G proteins that include Gs, Gi/o, Gq and G12/13 (27, 37-40). Low pH increased cAMP in CAFs but not in CAFs with GPR68 knockdown, a result implying linkage of GPR68 to Gs in CAFs (FIG. 6A). Moreover, the pH 6.8-promoted increase in IL-6 expression by CAFs was blocked by two PKA inhibitors (H89 and PKI), which did not alter GPR68 expression in CAFs (FIG. 6B). Low pH activation of GPR68 also increased ser131 phosphorylation (the PKA phosphorylation site) of the cAMP response element binding (CREB) protein (FIG. 6C). CREB inhibitors, naphthol AS-E (41) and 666-15 (42), disrupt CREB-CBP interaction and CREB-regulated gene expression and blunted pH 6.8-promoted IL-6 expression in CAFs without altering GPR68 expression (FIG. 6D).

Collectively, the data reveal a novel mechanism of bidirectional interaction between PDAC cells and CAFs (FIG. 7): PDAC cells release TNFα, which increases GPR68 expression in CAFs. Upon activation by extracellular protons, GPR68 up-regulates expression of IL-6, which is secreted from CAFs and can stimulate PDAC cell proliferation.

Prior studies have shown that GPCRs can regulate function in pancreatic cancer cells (43-46) but roles for GPCRs in CAFs, and in particular pancreatic CAFs, have not been known. Our use of Taqman GPCR arrays and RNA-seq as unbiased approaches to identify and quantify GPCRs in CAFs revealed that CAFs express a large number of GPCRs (47).

Figure 11:
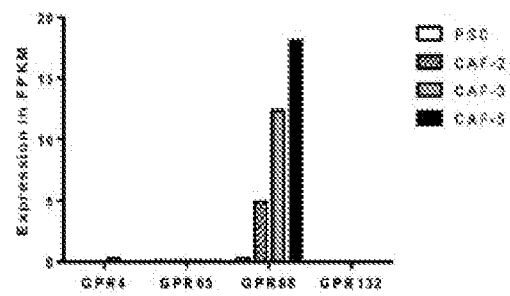
FIG. 11 shows an expression of proton-sensing GPCRs, GPR4, GPR65, GPR68 and GPR132 in PSCs and CAFs presented as FPKM values from data obtained by RNA-seq. GPR65 and GPR132 expression were not detected.

Several GPCRs were identified with increased expression in CAFs compared to that of PSCs and PFs but focused on GPR68 as a proton-sensing GPCR. GPR68 is nearly undetectable (TPM<0.1) in normal pancreas (FIG. 11). Similar results are also found in the Human Protein Atlas (48) and in single-cell analysis of PSCs from patients without cancer (49). Other GPCRs with increased expression in CAFs may also have roles in pancreatic cancer (50-54). There was no assessment for mutations of GPCRs since unlike PDAC cells, CAFs do not have somatic mutations (55).

Consistent with prior results (29), it was found that normal PSCs can be "instructed" by PDAC cells to become CAFs, at least in part via the action of TGFβ. Because TNFα but not TGFβ increases GPR68 expression in CAFs, the increase in fibrotic activity and up-regulation of GPR68 appear to be independent events in the transformation of PSCs to CAFs.

Immunohistochemistry of tissue from patients revealed GPR68 expression in the stroma and in PDAC cells, a result consistent with GPR68 expression in 3 PDAC cells lines, AsPC-1, BxPC-3 and MIA PaCa-2, (Table 5), which suggests that GPR68 might also regulate PDAC cell function. Perhaps in the development of pancreatic cancer PDAC cells and CAFs both utilize the acidic tumor microenvironment and GPR68 to regulate features of the malignant phenotype. CAFs from tumors besides PDAC express GPR68 and suggest roles for GPR68 in the acidic microenvironment of other types of tumors (56).

CAFs/activated PSCs, but not normal PSCs, release IL-6 (54) (FIG. 4). The data identify GPR68 as a previously unrecognized regulator of IL-6 production by CAFs and imply that this occurs via cAMP/PKA/CREB signaling. This effect is observed at both pH 7.4 and pH 6.8 (FIG. 5C) and perhaps contributes to elevated serum IL-6 levels in PDAC patients (57). Tumor-associated macrophages (58) and PDAC cells (59) also reportedly produce IL-6 in pancreatic cancer.

Treatments directed at the PDAC stroma in the tumor microenvironment have been controversial, especially data implying that stromal components can restrain tumor growth (60, 61). Two subgroups of CAFs have been identified in pancreatic tumors: one adjacent to PDAC cells and with elevated α-SMA expression while a second, located more distantly from the PDAC cells, secretes IL-6 (62). Based on those findings, the CAFs studied here, which express α-SMA and produce IL-6, are likely a mixture of the two types of CAFs.

These results identify GPR68 as a novel therapeutic target to blunt the activity of CAFs and thereby treat pancreatic cancer. More generally, CAFs in additional types of cancer may express GPR68 and utilize this GPCR as a means to respond to their acidic microenvironments and regulate the malignant phenotype.

FIGS. 1A-1E show myofibroblastic phenotype and GPCR expression of pancreatic CAFs. FIG. 1A is an immunoblot of α-SMA in PFs, PSCs and five primary CAF cell lines (CAF1 to 5); expression of α-SMA was normalized to that of GAPDH. FIG. 1B is a heat map of the selected CAF marker genes based on RNA-seq analysis of PSC and three primary CAF cell lines (CAF2, CAF3, and CAF5). Data are presented as log 2 fold-change of each CAF compared to PSC. Genes were categorized by four pro-fibrotic features: matrix proteins, stress fibers, cytokines and signaling proteins. FIG. 1C is a Tagman GPCR array analysis of non-chemosensory GPCR expression in five CAF lines. GPCR expression was quantified as the ΔCt between a GPCR and 18S rRNA; detected GPCRs were those with a ΔCt≤25. Table S1 lists the GPCRs detected in CAFs, PSCs, and PFs. FIG. 1D is an expression of 82 GPCRs detected in all five CAFs compared to PSCs and PFs. Expression difference was quantified as fold-change (fold change=2(ΔCtPSC or ΔCtPF-ΔCtCAF)). GPCRs were grouped as up-regulated (fold-change >2), down-regulated (fold-change <0.5), unchanged (0.5≤fold change ≤2), or uniquely expressed in CAFs (i.e., not detected in PSCs/PFs.) FIG. 1E is a log 2 fold-change of the 50 most abundant GPCRs in CAFs compared to PSCs as determined by RNA-seq plotted against the values from Taqman GPCR arrays; linear regressions and correlation coefficients are indicated.

Figure 2C:
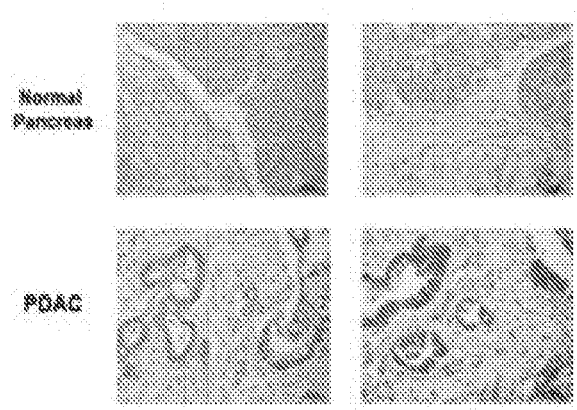
Figure 2D:
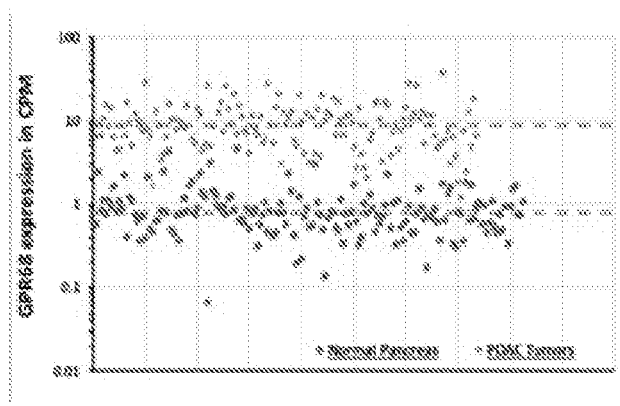
Figure 2E:
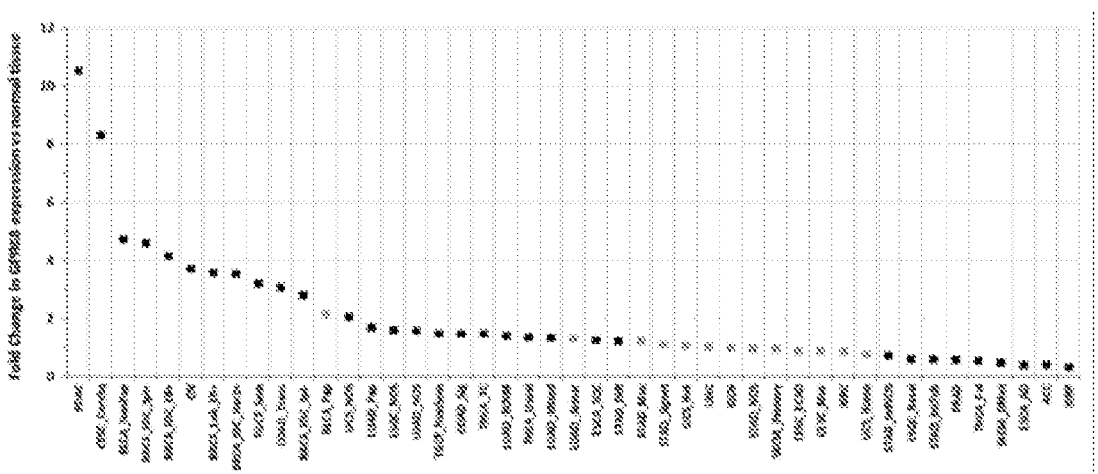

FIGS. 2A-2E show increased GPR68 mRNA and protein expression in pancreatic CAFs and PDAC tumors. FIG. 2A shows a real-time qPCR analysis of GPR68 expression in PSCs, PFs and CAFs1, 2, 3, 4, and 5. Expression of GPR68 was normalized to PFs by 2(ΔCtPF-ΔCtCAFs or ΔCtPSCs). Data shown are mean±SEM (n=3), unpaired t test, p<0.01, *p<0.001, ****p<0.0001. FIG. 2B shows an immunoblot of GPR68 in PFs, PSCs and five CAF cell lines 1 to 5; GPR68 expression was normalized to GAPDH. FIG. 2C is an immunohistochemistry of GPR68 in normal pancreatic tissues and in pancreases with PDAC. The top two panels are normal human pancreas; the stroma area is highlighted by red dotted lines. The bottom two panels are PDAC tissue; cancer cells are highlighted with yellow dotted lines. Increased GPR68 expression is seen in PDAC stromal cells and PDAC cells compared to control pancreas. FIG. 2D shows a GPR68 expression (Log 2 Counts per Million [CPM]) from RNA-seq data for PDAC tumors (from TCGA, n=147; orange dots) and normal pancreatic tissue (from GTEX, n=165; blue dots). GPR68 expression is 10.5-fold greater in PDAC tumors than normal tissue (FDR, False Discovery Rate=7.37E-233). Median expression for each cohort is shown (dashed lines). GPR68 expression in PDAC tumors is higher than median expression in normal tissue in all PDAC samples. FIG. 2E shows fold-changes in expression of GPR68 mRNA in 45 different types of tumors compared to normal tissue. Black squares indicate fold-changes that are (and gray squares that are not) statistically significant (FDR<0.05). GPR68 has the highest increase in expression in PDAC. The identity and number of replicates of each cancer type is in Table S4.

FIGS. 3A-3D show co-culture of PDAC cells and PSCs increases expression by PSCs of GPR68 and fibrotic genes, effects mediated by TNFα and TGFβ, respectively. FIG. 3A shows real-time qPCR analysis of gene expression in PSCs co-cultured for 48 h with three PDAC cell lines: AsPC-1, BxPC-3, and MIA PaCa-2. ΔCt values were normalized to 18S rRNA. Relative expression was compared by $2^{(\Delta Ct\ control-\Delta Ct co-culture)}$. Data are mean±SEM, n=3, unpaired t test, *p<0.05, p<0.01, *p<0.001, ****p<0.0001. FIG. 3B shows real-time qPCR analysis of gene expression in PSCs incubated for 48 h with TGFβ 1 or TNFα (each 50 ng/mL). Relative expression was compared by $2^{(\Delta Ct\ control-\Delta CtTGF\beta 1\ or\ \Delta CtTNF\alpha)}$. Data are mean±SEM, n=3, unpaired t test, *p<0.05, p<0.01, **p<0.0001. FIG. 3C shows real-time qPCR analysis of GPR68 expression in PSCs co-cultured for 48 h with AsPC-1, BxPC-3, and MIA PaCa-2 cells, with/without 10 ng/mL TNFα neutralizing antibody. Relative expression was compared to control by 2(ΔCt control-ΔCtco-culture). Data are mean±SEM, n=3, unpaired t test, *p<0.05. FIG. 3D shows real-time qPCR analysis of GPR68 expression in PSCs incubated for 6 h with TNFα (50 ng/mL) and NF-κB inhibitors, MG-132 (20 μM), IKK2 inhibitor VI (5 μM), JSH-23 (20 μM) and CAY10512 (0.3 μM). Relative expression was normalized to control by $2(\Delta Ct^{control-\Delta CtTGF\beta 1}\ or\ ^{\Delta CtTNF\alpha})$ n=3, data are mean±SEM, unpaired t test, *p<0.05, p<0.01, **p<0.0001.

Figure 4D:
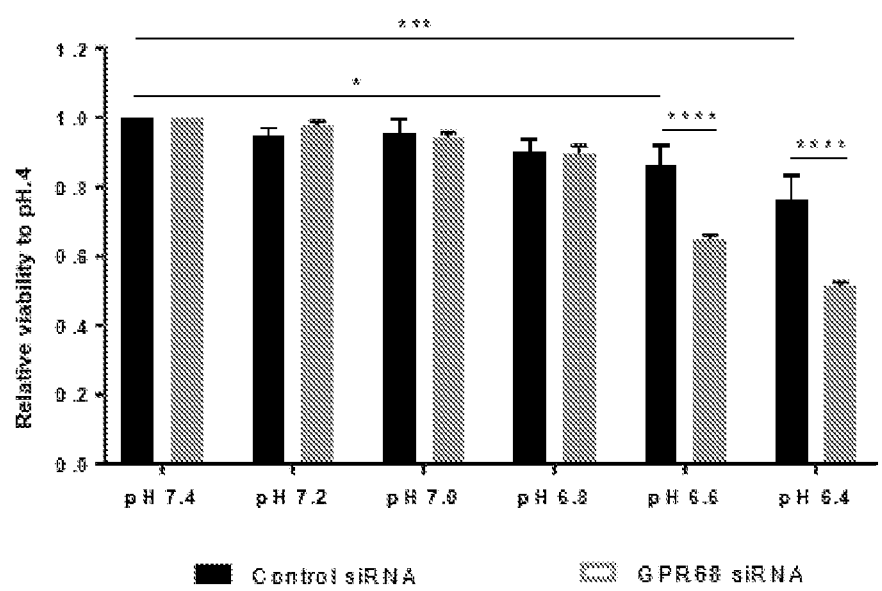

FIGS. 4A-4D shows gain-of-function of GPR68 in PSCs and loss-of-function studies of GPR68 in pancreatic CAFs. FIG. 4A shows PSCs transfected with GPR68 cDNA had increased GPR68 mRNA (bottom) and protein (top) expression compared to control (left panels). Real-time qPCR analysis of expression of fibrosis-related genes in PSCs transfected with control vector and GPR68 cDNA for 24 h. Expression was compared to the control vector. Data are mean±SEM, n=3, unpaired t test, *p<0.05, p<0.01. FIG. 4B show CAFs transfected with GPR68 siRNA had decreased GPR68 mRNA (bottom) and protein (top) expression compared to control (left panels). Real-time qPCR analysis of expression of fibrosis-related genes in CAFs transfected with control siRNA or GPR68 siRNA for 72 h. Expression was compared to control siRNA. Data are mean±SEM, n=3, unpaired t test, p<0.01, *p<0.001, **p<0.0001. FIG. 4C shows immunofluorescent staining of GPR68 and IL-6 in CAFs transfected with control siRNA or GPR68 siRNA for 72 h. Green: GPR68/IL6; Blue: DAPI. FIG. 4D show CAFs transfected with control or GPR68 siRNA were cultured at the indicated pH's for 48 h. Data for cell viability are presented relative to viability at pH 7.4. Data are mean±SEM, n=3, two-way ANOVA, *p<0.05, *p<0.001, **p<0.0001.

FIGS. 5A-5D shows the effect of growth at low pH and of GPR68 on gene expression and IL-6 expression by CAFs and PDAC cell proliferation. FIG. 5A shows real-time qPCR analysis of expression of fibrosis-related genes in CAFs cultured in pH 7.4 or 6.8 media for 6, 12 and 24 h. Expression was normalized to that at 0 h. Data are mean±SEM, n=3, unpaired t test, p<0.01, *p<0.001,

****p<0.0001. FIG. 5B show CAFs transfected with control or GPR68 siRNA were cultured in pH 7.4 or 6.8 media for 6 h. IL-6 expression was measured by real-time qPCR and normalized to expression with control siRNA at pH 7.4. Data are mean±SEM, n=3, two-way ANOVA, *p<0.05, p<0.01. FIG. 5C show CAFs transfected with control or GPR68 siRNA were cultured in pH 7.4 or 6.8 media for 24 h and 48 h. IL-6 in CM was assessed by ELISA. Data are mean±SEM, n=3, unpaired t test, **p<0.0001. FIG. 5D shows CEllTiter-Glo Luminescent (proliferation) assay of BxPC cells cultured in CM from CAFs transfected with control or GPR68 siRNA for 72 h with or without IL-6 neutralizing antibody. Data are mean±SEM, n=3, unpaired t test, *p<0.05, ***p<0.001.

FIGS. 6A-6D shows pH-dependent activation of GPR68, which acts via cAMP/PKA/CREB to increase IL6 production by pancreatic CAFs. FIG. 6A show CAFs transfected with control or GPR68 siRNA were cultured in pH media for 30 min, treated with 1 mM IBMX for 10 min and cellular cAMP was measured by the HitHunter cAMP assay. Data are mean±SEM, n=3, two-way ANOVA, *p<0.05, **p<0.0001. FIG. 6B shows real-time qPCR analysis of GPR68 and IL-6 expression in CAFs cultured for 6 h in pH 7.4 media, pH 6.8 media or pH 6.8 media in the presence of the PKA inhibitors, H89 and PKI. Results were normalized to those at pH 7.4. n=3, data are mean±SEM, unpaired t test, p<0.01, ***p<0.001, ns=non-significant. FIG. 6C shows immunoblot of CREB and phosphorylated CREB (p-CREB) of CAFs cultured in pH media (pH 7.4-6.4) for 6 h. Activation of CREB is shown as p-CREB/CREB. Data are mean±SEM, n=3, unpaired t test, *p<0.05. FIG. 6D shows real-time qPCR analysis of GPR68 and IL-6 expression in CAFs cultured for 6 h in pH 7.4, pH 6.8 media or pH 6.8 media in the presence of the CREB inhibitors, naphthol AS-E and 666-15. Results are normalized to those at pH 7.4. Data are mean±SEM, n=3, unpaired t test, p<0.01, *p<0.001, ns=non-significant.

Figure 7:
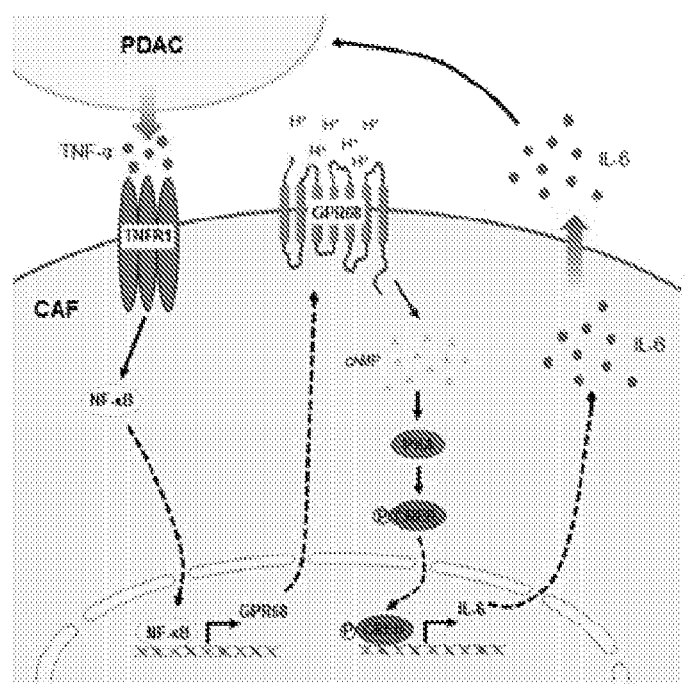
FIG. 7 shows a schematic summary of PDAC cell-CAF interaction and GPR68.

FIG. 7 shows a schematic summary of PDAC cell-CAF interaction and GPR68. PDAC cells release TNFα, which increases GPR68 expression by PSCs/CAFs. Extracellular protons activate GPR68 and increase IL-6 expression via the cAMP/PKA/CREB pathway. IL-6 secreted from CAFs can stimulate PDAC proliferation.

Tables 1A and 1B show GPCRs with the greatest increase in expression in CAFs compared to PSCs and PFs. The 10 GPCRs with the greatest increases in CAFs compared to PSCs (A) and PFs (B) are ranked by average fold-changes. Gene expression is presented as ΔCt (with 18S rRNA as reference in this and other experiments). The expression differences between CAFs and control cells were quantified as fold-changes ($2^{(\Delta CtPSC \text{ or } \Delta CtPF - \Delta CtCAF)}$) Average ΔCt in CAFs was calculated by Log 2 of mean fold-changes. Tables 3 and 4 compare the commonly detected 82 GPCRs in CAFs with PSCs and PFs, respectively.

Table 2 shows Taqman GPCR array data of the 82 non-chemosensory GPCRs commonly expressed by CAFs isolated from five PDAC patients and ranked from highest to lowest expressed. Expression of each GPCR was quantified as ΔCt value relative to that of 18S rRNA. Detected GPCRs had ΔCt values equal or less than 25. The average ΔCt values were calculated as the Log 2 of mean fold-changes relative to 18S rRNA. The primary G protein linkage for each GPCR was assigned according to the IUPHAR database (63).

Table 3 shows a comparison of the 82 commonly detected GPCRs expressed by CAFs with their expression by PSCs. Expression is presented as ΔCt relative to that of 18S rRNA. The expression difference between CAFs from each of 5 patients and PSCs was quantified as fold change ($2^{(\Delta CtPSC - \Delta CtCAF)}$) GPCRs were grouped into 4 categories according the average fold-change values: Up-regulated in CAFs (Average fold change >2), Down-regulated in CAFs (Average fold-change <0.5), unchanged in CAFs (0.5<Average fold-change <2), and Uniquely expressed in CAFs (i.e., ΔCt>25 in PSCs).

Table 4 shows a comparison of the 82 commonly detected GPCRs expressed by CAFs with their expression by PFs. Expression is shown as ΔCt relative to that of 18S rRNA. The expression difference between CAFs from each of 5 patients and PFs was quantified as fold-change (2(ΔCtPF-ΔCtCAF)). GPCRs were grouped into 4 categories according to the average fold-change values: Up-regulated in CAFs (Average fold-change >2), Down-regulated in CAFs (Average fold-change <0.5), Unchanged in CAFs (0.5<Average fold-change <2), and Uniquely expressed in CAFs (i.e., ΔCt>25, in PFs).

Table 5 shows tumor types (and their abbreviations) assessed and numbers of replicates. Differential Expression (DE) was done and the Table adapted from the Insel lab GPCRs in cancer project (insellab.github.io). In brief, gene expression from tumors (TCGA) and normal tissues (GTEX), expressed in RSEM (64) expected counts, was downloaded from xena.ucsc.edu. The data were analyzed via the TOIL pipeline (65) such that TCGA and GTEX samples were analyzed together using the same bioinformatics pipeline. For each tumor type, a matrix with the counts data for tumor and normal tissue was input to EDGER (61) and fold-changes and FDR were obtained. Gene expression in CPM (Counts per Million) was also obtained from EDGER.

FIG. 8 shows a heat map of the log 2 of fold-changes of GPCRs expressed by each of 3 CAF samples compared to PSCs, as assayed using GPCR arrays and RNA-seq. GPCR expression by CAFs is listed from the highest (top) to lowest expressed (bottom). GPCRs not detected in PSCs (i.e., ΔCt>25) were excluded from this plot.

FIG. 9 shows a public RNA-seq data mined for analysis of GPR68 expression. Samples labelled CA are from activated PSCs/CAFs of PDAC patients while samples labelled DI are from PSCs of patients without PDAC (12). hPSC and CAFs 2, 3, and 5 connote our RNA-seq data from this study. One PSC sample (sample ID: DI2) was excluded from the analysis due to anomalous expression of multiple GPCRs. Analysis via EdgeR revealed that differences in GP68 expression are highly significant (P-value=5.48E-06, FDR [False Discovery Rate]=0.0044).

FIGS. 10A-10F shows immunohistochemistry of GPR68 in normal pancreatic tissues and in pancreas with PDAC. FIGS. S7A and S7B are normal human pancreatic tissue; the stromal cells are negative for GPR68 in stromal area, as highlighted by red dotted lines. FIGS. S7C and S7D are PDAC tumors with medullary invasion. Tumor area are marked as "T", and the stromal cell area (inside the red dotted lines) is negative or weakly positive for GPR68. FIGS. S7E and S7F are PDAC tumors with scirrhous-type invasion. Increased GPR68 expression was detected in PDAC stromal cells (arrowheads) in the stromal area (bounded by red dotted lines). GPR68 was also expressed in PDAC cells. N; normal pancreatic acinar cells, T; PDAC cells.

FIG. 11 shows an expression of proton-sensing GPCRs, GPR4, GPR65, GPR68 and GPR132 in PSCs and CAFs presented as FPKM values from data obtained by RNA-seq. GPR65 and GPR132 expression were not detected.

Figure 12:
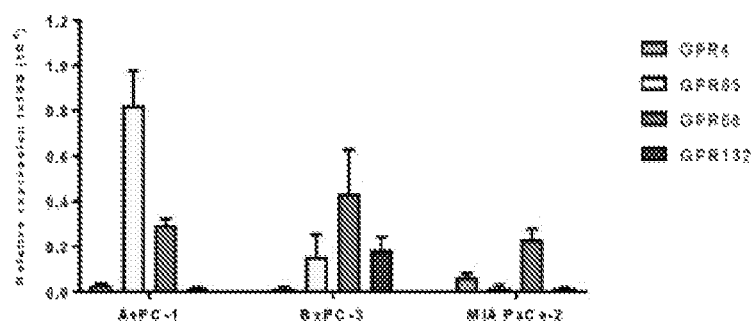
FIG. 12 shows a real-time qPCR analysis of expression of the four proton-sensing GPCRs (GPR4, GPR65, GPR68 and GPR132) in PDAC cell lines: AsPC-1, BxPC-3 and MIA PaCa-2.

FIG. 12 shows a real-time qPCR analysis of expression of the four proton-sensing GPCRs (GPR4, GPR65, GPR68 and GPR132) in PDAC cell lines: AsPC-1, BxPC-3 and MIA PaCa-2. Gene expression was measured as ΔCt values using 18S rRNA as the reference gene. Relative expression to 18S was calculated as 2(−ΔCt). Data are mean±SEM.

Figure 13:
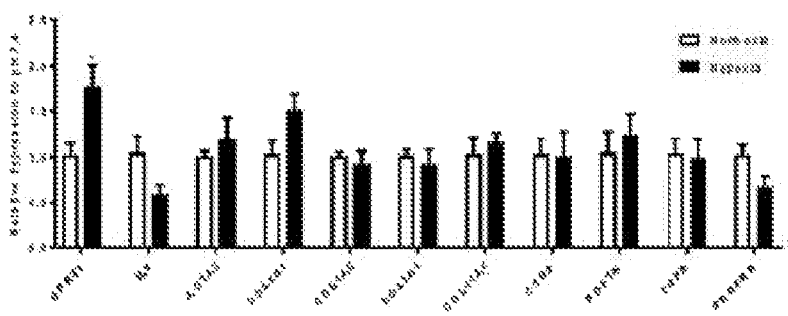
FIG. 13 shows a real time qPCR analysis of gene expression change in PSCs cultured in normoxia (21% O2) and hypoxia (1% O2) for 48 h. Gene ΔCt values were calculated based on expression of 18S rRNA.

FIG. 13 shows a real time qPCR analysis of gene expression change in PSCs cultured in normoxia (21% $O_2$) and hypoxia (1% $O_2$) for 48 h. Gene ΔCt values were calculated based on expression of 18S rRNA. Relative expression was normalized to normoxia. Data are means SEM, n=3. Unpaired t test, *p<0.05.

Figure 14:
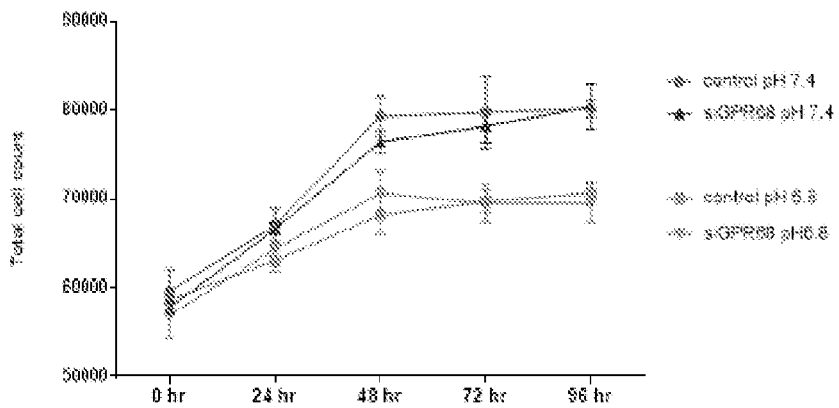
FIG. 14 shows CAFs and CAFs with GPR68 knockdown were cultured in pH 7.4 or pH 6.8 media up to 96 h.

FIG. 14 shows CAFs and CAFs with GPR68 knockdown were cultured in pH 7.4 or pH 6.8 media up to 96 h. Cells were stained with Trypan blue and counted by a hemocytometer every 24 h. n=2, data are mean±SD.

Figure 15:
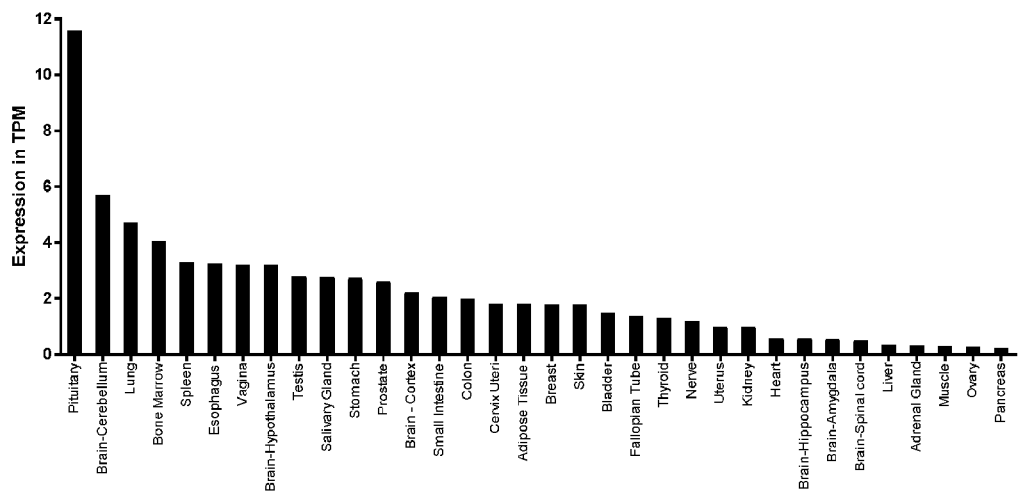
FIG. 15 shows expression of GPR68 in normal human tissues presented in TPM.

FIG. 15 shows expression of GPR68 in normal human tissues presented in TPM. Data were obtained from the UCSC Xena tool (xena.ucsc.edu), from analysis via the TOIL pipeline (65) for samples from the GTEX database. Data are presented as median values. Of the tissues studied, normal pancreas has the lowest expression of GPR68.

FIGS. 16A-16C show that GPRC5A and GPR68 are highly expressed in PDAC tumors with median, upper and lower quartile expression values (indicated by the error bars) for GPRC5A and GPR68 in PDAC tumors (The Cancer Genome Atlas [TCGA]) database, n=147 patient samples) and in normal pancreatic tissue (GTEx datatbase, n=165 patient samples). GPRC5A is increased ~50-fold (FDR<<0.05) and GPR68 is increased ~10-fold (FDR<<0.05) in PDAC tumors compared to normal pancreatic tissue. (B) Mean (and SEM) expression of GPRC5A and GPR68 in PDAC tumors (in TCGA) with tumor grades G1, G2, and G3. (C) Mean (and SEM) expression of GPRC5A and GPR68 in TCGA PDAC tumors from males and females. The small expression differences for tumor grades and between males and females are not statistically significant.

Material and Methods
Cell Isolation and Culture

Patient-derived PDAC tumors were diced into small pieces (0.3-0.5 mm) and embedded in growth factor reduced Matrigel on a 60 mm culture dish. Pre-warmed CAF medium (4.5 g/L glucose Dulbecco's Modified Eagle's Medium (DMEM), 30% fetal bovine serum (FBS), 1 ug/ml fetuin, 20 ng/ml EGF, 2 mM glutamate, 1 mM sodium pyruvate, non-essential amino acids (AAs), 100 I.U./ml penicillin (pen), 100 µg/ml streptomycin (strep), 0.25 µg/ml amphotericin B) was added to immerse the Matrigel. Cells were incubated in 95% air/5% CO2.

After ~6 d, explants with CAF outgrowth were harvested, suspended in phosphate-buffered saline (PBS) and incubated at room temperature (RT) with 0.025% trypsin for 15 min. Cells collected by centrifugation at 1000×g for 5 min were resuspended, transferred to and cultured on 10 cm plates with CAF media. Primary CAFs can be cultured for 10-15 passages before senescence occurs; we used only low passage (<15) primary CAFs. PSCs and PFs were purchased from Sciencell Research Laboratories (Carlsbad, Calif., USA, Cat. #3830) and Vitro Biopharma (Golden, Colo., USA, Cat. #SC00A5), respectively and grown via the manufacturers' instructions. PDAC cell lines, AsPC-1, BxPC-3 and MIA PaCa-2, were purchased from American Type Culture Collection. AsPC-1 and BxPC-3 were cultured in RPMI-1640 media with 10% FBS, nonessential AAs, sodium pyruvate and pen-strep. MIA PaCa-2 was grown in 4.5 g/L DMEM media with 10% FBS, nonessential AAs, sodium pyruvate and pen-strep. Cells were grown at 37° C. with 95% air/5% CO2.

Taqman GPCR Array

Cells were cultured on 6-well plates until ~80% confluent, then washed twice with cold PBS. RNA was isolated using an RNeasy kit with DNase treatment (Qiagen, Valencia, Calif., USA) and converted to cDNA using SuperScript III (Invitrogen, Gran Island, N.Y., USA), according to the manufacturer's protocol. cDNA was diluted with ddH2O and mixed with Taqman reaction buffer to a final concentration of 1 µg/mL. GPCR expression was assayed using Taqman GPCR Arrays (Applied Biosystems, Life Technologies Corp., Carlsbad, Calif., USA, Cat. #4367785) by a 7900HT Fast Real-Time system (Applied Biosystems). Data were analyzed by RQ Manager software (Applied Biosystems). GPCR expression was quantified as ΔCt with 18S rRNA as reference gene. Comparison of expression by different cells was quantified as fold-change=2(ΔΔCt).

RNA-seq

RNA extracted from CAFs and PSCs underwent RNA sequencing by DNA Link Inc. (San Diego, Calif., USA). Libraries were prepared using the Illumina Truseq stranded mRNA kit and sequenced at ~25-30 million 75 base single reads per sample on an Illumina Nextseq500 sequencer. FASTQ files were aligned using the STAR aligner (21) on Illumina's Basespace cloud computing/analysis service, with reads mapped to the human hg38 reference genome (refseq). BAM files with aligned reads were analyzed using Cufflinks v2.2.1.0 (22, 23) via Galaxy to quantify gene expression in FPKM (Fragments Per Kilobase of transcript per Million mapped reads). Cufflinks effective length correction was used for length normalization, along with multi-read corrections; fragments compatible with specified reference RNAs were counted to calculate FPKM's. Counts files generated by the STAR Basespace Application were input into edgeR (24) to determine CPM (counts per million) and perform differential expression (DE) analysis. Pairwise comparison of fold-changes of GPCR expression in individual CAF samples with that in PSCs was calculated from their ratio of CPM values.

Data Mining of Public RNA-Seq Data

Archived data in the public domain stored on the NCBI GEO repository (25) were mined to obtain additional gene expression data. RNAseq data (12), stored at accession number GSE43770 in SRA format were mined for expression of GPCRs in human PSCs. SRA files were imported into Illumina's Basespace platform and extracted FASTQ files were analyzed using the same bioinformatics analysis pipeline as above, to quantify gene expression in FPKM and CPM.

Real-Time qPCR

RNA isolated using an RNeasy kit with DNase treatment (Qiagen) and converted to cDNA using an iScript cDNA Synthesis Kit (Bio-Rad, Irvine, Calif., USA). cDNA was mixed with gene-specific primers and SYBR green reagent (Quanta Biosciences, Gaithersburg, Md., USA) for PCR amplification using a DNA Engine Opticon 2 system (MJ Research, Waltham, Mass., USA). Primers were designed using Primer Premier 6 software (PREMIER Biosoft, Palo Alto, Calif., USA). Gene expression was quantified as ΔCt using 18S rRNA as the reference gene. Expression of different cells was compared as fold-change=2(ΔΔCt). RNA isolated using an RNeasy kit with DNase treatment (Qiagen) and converted to cDNA using an iScript cDNA Synthesis Kit (Bio-Rad, Irvine, Calif., USA). cDNA was mixed with gene-specific primers and SYBR green reagent (Quanta Biosciences, Gaithersburg, Md., USA) for PCR amplification using a DNA Engine Opticon 2 system (MJ Research, Waltham, Mass., USA). Primers were designed using Primer Premier 6 software (PREMIER Biosoft, Palo Alto, Calif., USA). Gene expression was quantified as ΔCt using 18S rRNA as the reference gene. Expression of different cells was compared as fold-change=2(AACt). The primer sequences are: 18S-F: 5'-GCCGTTCTTAGTTGGTGGAG-3' (SEQ ID NO: 1); 18S-R: 5'-TCACAGACCTGTTAT-TGCTCAA-3' (SEQ ID NO: 2); GPR68-F: 5'-CCTTCCGCTTCCACCAGTT-3' (SEQ ID NO: 3); GPR68-R: 5'-TCGTCCTCGATGACCTCCT-3' (SEQ ID NO: 4); ACTA2-F: 5'-TTACTACTGCTGAGCGTGAGAT-3' (SEQ ID NO: 5); ACTA2-R: 5'-CAT-GATGCTGTTGTAGGTGGTT-3' (SEQ ID NO: 6); COL1A1-F: 5'-TCGGAGGAGAGTCAGGAAGG-3' (SEQ ID NO: 7); COL1A1-R: 5'-CAGCAACACAGTTA-CACAAGGA-3' (SEQ ID NO: 8); IL6-F: 5'-ACAGC-CACTCACCTCTTCAG-3' (SEQ ID NO: 9); IL6-R: 5'-GCAAGTCTCCTCATTGAATCCA-3' (SEQ ID NO: 10); COL3A1-F: 5'-GCTGGCTACTTCTCGCTCT-3' (SEQ ID NO: 11); COL3A1-R: 5'-TCTCTATCCGCAT-AGGACTGAC-3' (SEQ ID NO: 12); POSTN-F: 5'-ACGGTGCGATTCACATATTCC-3' (SEQ ID NO: 13); POSTN-R: 5'-TAATGTCCAGTCTCCAGGTTGT-3' (SEQ ID NO: 14); CTGF-F: 5'-ACATTAGTA-CACAGCACCAGAA-3' (SEQ ID NO: 15); CTGF-R: 5'-GCTACAGGCAGGTCAGTGA-3' (SEQ ID NO: 16); PDGFRB-F: 5'-GGAATGAGGTGGTCAACTTCG-3' (SEQ ID NO: 17); PDGFRB-R: 5'-GGATGGAGCG-GATGTGGTAA-3' (SEQ ID NO: 18). Gene expression was quantified as ΔCt using 18S rRNA as the reference gene. We compared expression of different cells as fold-change=2 (AACt).

Transfection and siRNA Knockdown

For transfection, we mixed 2 μg of an empty pLX304 vector or a pLX304 vector containing GPR68 (DNASU Plasmid Repository, Tempe, Ariz., USA) with 8 μL FuGENE HD transfection reagent (Promega Corp.; Madison, Wis., USA) in Opti-MEM reduced serum media at RT for 15 min. DNA:transfection reagent complex (100 μL) was added to PSCs and incubated for 24h.

For GPR68 knockdown, siGENOME non-targeting control siRNA and SMARTpool human GPR68 siRNA (mixture of 4 GPR68 siRNAs) was purchased from GE Dharmacon (Lafayette, Colo., USA). CAFs were cultured overnight in 6-well plates (80,000 cells/well); 2.25 mL of fresh CAF media were then added to each well, followed by 250 μl of opti-MEM media containing 7.5 μL lipofectamine reagent and 25 pmol of siRNA (final concentration=10 nM). The cells were then incubated for 72 h.

Immunoblot Analysis

Lysates were collected from cells grown in 6-well plates by scraping wells in 80 μL RIPA buffer (Cell Signaling Technology, Danvers, Mass., USA) containing phosphatase and protease inhibitors. Cell lysates were homogenized by sonication. Protein concentrations were determined by BCA protein assay (ThermoFisher Scientific, Waltham, Mass., USA). Proteins were separated by SDS/PAGE in 4-12% polyacrylamide gels (Invitrogen) and transferred gels to PVDF membranes using an iBLOT transfer machine (Invitrogen). Membranes were blocked using 5% BSA (w/v) in PBS Tween-20 (PBST) and incubated at 4° C. overnight with primary antibodies diluted in 1% BSA (w/v) in PBST. Blots were then incubated with secondary antibodies conjugated with horseradish peroxidase at RT for 1 h. Bands were visualized by adding chemiluminescent substrate (LUMI-GEN, Southfield, Mich., USA). Densitometry quantification was analyzed by Image J software (NIH). Antibodies used in this study were for α-SMA (A5228, Sigma-Aldrich, St. Louis, Mo.); GPR68 (sc-98437, Santa Cruz Biotechnology, Dallas, Tex., USA); phospho-CREB (Ser133) (9198S, Cell Signaling Tech.) and CREB (sc-377154, Santa Cruz Biotech.).

Immunofluorescence Staining

CAFs (without or with GPR68 knockdown) were seeded on 12 mm round coverslips (Corning, Corning, N.Y.) in 24-well plates (20,000 cells/well) and incubated overnight. Wells were washed twice with PBS, fixed in 2% paraformaldehyde/PBS for 10 min, and then washed with 10 mM Glycine (pH7.4) in PBS for 5 min. The cells were permeabilized in 0.1% TritonX/PBS for 10 min at RT. After washing with PBS/Tween 20 (0.1% Tween), the coverslips were blocked by addition of 1% BSA/PBS/0.05% Tween for 20 min at RT. Primary antibodies were diluted in 1% BSA/PBS/0.05% Tween 20 with 1:100 ratio for GPR68 antibody (H-75, Santa Cruz Biotechnology) and 1:1000 ratio for IL-6 antibody (ab9324, Abcam, Cambridge, Mass., USA) Coverslips were incubated with diluted primary antibodies for 48 h at 4° C. After 3 washes with 1% BSA/PBS/0.05% Tween, the coverslips were incubated with secondary antibodies atRT for 1 h and with DAPI for nuclear staining. Images were obtained using a Zeiss AxioObserver D1 microscope equipped with an LD A-Plan 20X/0.35 Ph objective.

Immunohistochemistry

Paraffin-embedded tissue was sectioned and placed in a microwave oven for 5 min for antigen retrieval. Immunostaining for GPR68 was performed using an automated immunostainer (DAKO Japan, Tokyo) with anti-GPR68 rabbit polyclonal antibody (ab61420, Abcam), peroxidase-labeled secondary antibodies and diaminobenzidine (DAB) as substrate.

Co-Culture of PSCs with PDACs

PSCs were cultured overnight on 6-well plates (50,000 cells/well). AsPC-1, BxPC-3 and MIA PaCa-2 cells were cultured overnight (80,000 cells/well) on 24 mm 6-well Transwell permeable supports that have a 0.4 μm pore size (Corning, Corning, N.Y., USA). The next day the Transwell supports were placed on top of PSCs and cultured for 48 h in 4.5 g glucose/L DMEM media with pen-strep in the absence or presence of 10 ng/mL TNFα neutralizing antibody (InvivoGen, San Diego, Calif., USA). PSCs were then removed for mRNA purification and qPCR.

Cell Viability Assay

The pH media are DMEM containing 5 g/L glucose, 20 mM HEPES, 20 mM NaHCO$_3$, 2% FBS, 100 I.U./ml penicillin and 100 μg/ml streptomycin, pH adjusted by HCl or NaOH at room temperature. CAFs transfected with control or GPR68 siRNA were grown overnight in 96-well plates (10,000 cells/well). The cells were then incubated for 48 h in low serum pH media. Cell viability were assessed by a CEllTiter-Glo Luminescent assay (Promega) and detected using a DXT 800 multimode plate reader (Beckman Coulter, Carlsbad, Calif., USA).

Cell Proliferation Assay

CAFs were placed onto 6-well plates (80,000 cells/well) and transfected with control or GPR68 siRNA for 72 h. Cell culture media were then changed to pH media and continue incubation for 48 h. CM were passed through a 0.45 m filter, incubated with 10 ng/mL IL6 neutralizing antibody (InvivoGen, San Diego, Calif., USA) for 30 min and then added to BxPC-3 cells seeded in 96-well plates (10,000 cells/well).

The BxPC-3 cells were cultured with CAF CM for 72 h. Cell proliferation were assessed by a CEllTiter-Glo Luminescent assay (Promega) and detected using a DXT 800 multimode plate reader.

IL-6 ELISA

CAF CM was collected as just above, assayed IL-6 protein using Human IL-6 ELISA MAX™ standard set (BioLegend, San Diego, Calif., USA) using the manufacturer's protocol and detected absorbance at 450 nm with a DXT 800 multimode plate reader.

cAMP Assay

CAFs transfected with control or GPR68 siRNA were grown overnight on a 96-well plate (10,000 cells/well). Culture media were changed to pH media with a pH between 6.4 and 7.4 and incubated for 30 min.

Isobutylmethylxanthine (IBMX, 1 mM final concentration, a cyclic nucleotide phosphodiesterase inhibitor), was added to each well. Cells were incubated (37° C.) for additional 10 min prior to quantifying cAMP by use of the HitHunter cAMP assay (DiscoverX, Fremont, Calif., USA) with detection of the luminescent signals by a DXT 800 multimode plate reader.

Statistical Analysis

Data were analyzed using GraphPad Prism 6.0 software (GraphPad Software, La Jolla, Calif., USA). Data are presented as mean±SEM. Statistical comparisons were calculated by two-tailed unpaired t-test or two-way ANOVA. $P<0.05$ values were considered statistically significant.

Data Availability

RNA-seq FASTQ files and gene expression data in FPKM that support the findings of this study have been deposited in NCBI GEO with the accession code GSE101665.

TABLE 1A

Highest increase GPCR expression compared to PSG

| | Fold-changes | | | | | | |
|---|---|---|---|---|---|---|---|
| GPCR | CAF1 vs. PSC | CAF2 vs. PSC | CAF3 vs. PSC | CAF4 vs. PSC | CAF5 vs. PSC | Avg. Fold-changes | Avg. ΔCt in CAFs |
| OXTR | 790.2 | 128.0 | 35.2 | 284.2 | 113.6 | 270.2 | 15.6 |
| GPR68 | 20.3 | 18.5 | 68.8 | 55.4 | 118.4 | 56.3 | 17.5 |

TABLE 1A-continued

Highest increase GPCR expression compared to PSG

| | Fold-changes | | | | | | |
|---|---|---|---|---|---|---|---|
| GPCR | CAF1 vs. PSC | CAF2 vs. PSC | CAF3 vs. PSC | CAF4 vs. PSC | CAF5 vs. PSC | Avg. Fold-changes | Avg. ΔCt in CAFs |
| GPR56 | 2.6 | 1.7 | 69.2 | 4.1 | 150.9 | 45.7 | 18.7 |
| GPRC5A | 59.8 | 4.9 | 49.7 | 71.7 | 33.8 | 44.0 | 15.2 |
| SSTR1 | 29.4 | 9.4 | 27.9 | 66.8 | 76.1 | 41.9 | 17.2 |
| BDKRB1 | 3.1 | 13.0 | 13.1 | 25.8 | 50.5 | 21.1 | 16.6 |
| PPYR1 | 8.3 | 60.4 | 4.1 | 4.9 | 17.1 | 18.9 | 19.7 |
| GPR37 | 4.5 | 30.9 | 0.7 | 43.3 | 1.6 | 16.2 | 18.7 |
| BDKRB2 | 1.2 | 10.4 | 11.8 | 20.6 | 32.2 | 15.2 | 18.5 |
| ADRB2 | 11.2 | 1.0 | 2.7 | 38.4 | 12.7 | 13.2 | 20.0 |

TABLE 1B

Highest increase GPCR expression compared to PFs

| | Fold changes | | | | | | |
|---|---|---|---|---|---|---|---|
| GPCR | CAF1 vs. PF | CAF2 vs. PF | CAF3 vs. PF | CAF4 vs. PF | CAF5 vs. PF | Avg. Fold-changes | Avg. ΔCt in CAFs |
| GPR56 | 3.5 | 2.2 | 91.6 | 5.4 | 199.7 | 60.5 | 18.7 |
| GPR68 | 7.0 | 6.4 | 23.8 | 19.1 | 40.9 | 19.4 | 17.5 |
| F2RL1 | 1.9 | 0.8 | 17.4 | 4.4 | 59.0 | 16.7 | 16.4 |
| EDG1 | 12.2 | 5.8 | 4.3 | 3.9 | 54.4 | 16.1 | 19.5 |
| SSTR1 | 10.3 | 3.3 | 9.7 | 23.3 | 26.5 | 14.6 | 17.2 |
| GPRC5A | 19.5 | 1.6 | 16.2 | 23.4 | 11.1 | 14.4 | 15.2 |
| GPR51 | 0.8 | 3.6 | 1.8 | 19.8 | 31.9 | 11.6 | 19.4 |
| FZD4 | 12.4 | 5.5 | 11.7 | 16.0 | 10.2 | 11.2 | 16.8 |
| GPR150 | 7.8 | 2.7 | 5.5 | 16.6 | 22.1 | 11.0 | 21.2 |
| F2RL2 | 6.9 | 18.9 | 6.4 | 4.4 | 15.2 | 10.4 | 20.1 |

TABLE 2

Taqman GPCR array data of the 82 non-chemosensory GPCRs commonly expressed by CAFs isolated from five PDAC patients and ranked highest to lowest expressed

| | GPCR | CAF14 ΔCt | CAF2 ΔCt | CAF3 ΔCt | CAF4 ΔCt | CAF5 ΔCt | Avg. CAF ΔCt | STD DEV | Primarylink age |
|---|---|---|---|---|---|---|---|---|---|
| 1 | F2R | 13.8 | 14.8 | 13.5 | 12.9 | 12.6 | 13.3 | 0.8 | Gi/Go, Gq/G11, G12/G13 |
| 2 | GPR176 | 14.4 | 15.8 | 15.4 | 14.3 | 15.4 | 14.9 | 0.6 | Unknown |
| 3 | GPRC5A | 14.7 | 18.3 | 15.0 | 14.5 | 15.5 | 15.2 | 1.4 | Unknown |
| 4 | LPHN2 | 16.3 | 17.2 | 14.4 | 15.9 | 14.5 | 15.3 | 1.1 | Unknown |
| 5 | OXTR | 14.0 | 16.7 | 18.5 | 15.5 | 16.8 | 15.6 | 1.5 | Gq/G11 |
| 6 | FZD6 | 15.7 | 16.3 | 17.0 | 14.8 | 16.1 | 15.8 | 0.7 | Gi/Go, Gq/G11 |
| 7 | EDG2 | 15.9 | 16.7 | 16.3 | 15.0 | 15.6 | 15.8 | 0.6 | Gi/Go, Gq/G11, G12/G13 |
| 8 | FZD1 | 17.2 | 17.9 | 15.6 | 16.3 | 15.3 | 16.2 | 1.0 | Gi/Go, Gq/G11 |
| 9 | GPR124 | 16.5 | 15.3 | 17.6 | 16.2 | 17.0 | 16.3 | 0.8 | Unknown |
| 10 | F2RL1 | 19.5 | 20.8 | 16.4 | 18.3 | 14.6 | 16.4 | 2.2 | Gq/G11 |
| 11 | BDKRB1 | 19.4 | 17.3 | 17.3 | 16.3 | 15.4 | 16.6 | 1.3 | Gi/Go, Gq/G11 |
| 12 | CD97 | 16.6 | 16.8 | 17.4 | 16.7 | 16.3 | 16.7 | 0.4 | G12/G13 |
| 13 | FZD4 | 16.7 | 17.8 | 16.7 | 16.3 | 16.9 | 16.8 | 0.5 | G12/G13 |
| 14 | C11ORF4 | 17.1 | 18.2 | 17.3 | 16.3 | 16.1 | 16.8 | 0.7 | Unknown |
| 15 | CHRM2 | 17.2 | 16.5 | 23.1 | 15.4 | 18.7 | 16.8 | 2.7 | Gi/Go |
| 16 | SSTR1 | 17.7 | 19.3 | 17.8 | 16.5 | 16.3 | 17.2 | 1.1 | Gi/Go |
| 17 | ELTD1 | 17.0 | 19.2 | 17.3 | 17.6 | 16.3 | 17.2 | 1.0 | Unknown |
| 18 | FZD2 | 17.0 | 16.9 | 17.5 | 17.4 | 17.8 | 17.3 | 0.3 | Gi/Go |

TABLE 2-continued

Taqman GPCR array data of the 82 non-chemosensory GPCRs commonly expressed by CAFs isolated from five PDAC patients and ranked highest to lowest expressed

| | GPCR | CAF14 ΔCt | CAF2 ΔCt | CAF3 ΔCt | CAF4 ΔCt | CAF5 ΔCt | Avg. CAF ΔCt | STD DEV | Primary linkage |
|---|---|---|---|---|---|---|---|---|---|
| 19 | EDNRA | 18.9 | 18.6 | 17.9 | 17.5 | 15.9 | 17.3 | 1.1 | Gq/G11 |
| 20 | PTGIR | 17.3 | 19.0 | 19.5 | 16.2 | 17.4 | 17.4 | 1.2 | Gs |
| 21 | EDNRB | 21.7 | 18.6 | 20.4 | 15.6 | 17.8 | 17.4 | 2.1 | Gs, Gi/Go, Gq/G11 |
| 22 | GPR68 | 19.0 | 19.1 | 17.2 | 17.5 | 16.4 | 17.5 | 1.0 | Gi/Go, Gq/G11 |
| 23 | GABBR1 | 18.4 | 18.5 | 18.6 | 17.4 | 17.5 | 18.0 | 0.5 | Unknown |
| 24 | LGR4 | 19.1 | 19.6 | 16.6 | 18.7 | 18.0 | 18.0 | 1.0 | Unknown |
| 25 | FZD8 | 19.4 | 19.0 | 17.3 | 18.4 | 17.3 | 18.0 | 0.9 | Unknown |
| 26 | GPR125 | 18.8 | 19.4 | 18.4 | 18.5 | 17.5 | 18.4 | 0.6 | Unknown |
| 27 | GPR126 | 18.4 | 19.5 | 18.6 | 17.9 | 18.3 | 18.5 | 0.6 | Unknown |
| 28 | GPR153 | 18.0 | 18.8 | 19.0 | 17.9 | 19.2 | 18.5 | 0.6 | Unknown |
| 29 | MRGPRF | 18.8 | 18.2 | 18.3 | 19.2 | 18.3 | 18.5 | 0.4 | Unknown |
| 30 | BDKRB2 | 22.3 | 19.1 | 18.9 | 18.1 | 17.5 | 18.5 | 1.7 | Gs, Gi/Go, Gq/G11 |
| 31 | F2D7 | 17.8 | 18.3 | 17.9 | 20.7 | 20.6 | 18.6 | 1.3 | Gs, Gi/Go |
| 32 | GPR56 | 22.8 | 23.5 | 18.1 | 22.2 | 16.9 | 18.7 | 2.6 | Gq/G11, G12/G13 |
| 33 | GPR37 | 20.5 | 17.7 | 23.3 | 17.3 | 22.0 | 18.7 | 2.3 | Gi/Go |
| 34 | OPN3 | 18.8 | 18.5 | 21.4 | 17.8 | 19.3 | 13.8 | 1.2 | Unknown |
| 35 | SMO | 18.5 | 20.9 | 18.8 | 19.6 | 19.0 | 19.1 | 0.9 | Gi/Go, G12/G13 |
| 36 | TBXA2R | 19.1 | 20.2 | 19.8 | 19.0 | 18.5 | 19.2 | 0.6 | Gq/G11 |
| 37 | GPR161 | 19.6 | 19.5 | 20.0 | 19.0 | 18.7 | 19.3 | 0.5 | Unknown |
| 38 | GPR51 | 23.3 | 21.1 | 22.1 | 18.6 | 17.9 | 19.4 | 2.0 | Unknown |
| 39 | GPR173 | 19.2 | 20.5 | 19.5 | 19.9 | 18.8 | 19.5 | 0.6 | Unknown |
| 40 | EDG1 | 19.9 | 21.0 | 21.4 | 21.6 | 17.8 | 19.5 | 1.4 | Gi/Go |
| 41 | EDG3 | 19.3 | 19.9 | 19.6 | 19.4 | 20.1 | 19.6 | 0.3 | Gi/Go, Gq/G11, G12/G13 |
| 42 | PPYR1 | 20.9 | 18.0 | 21.9 | 21.6 | 19.8 | 19.7 | 1.4 | Gi/Go |
| 43 | ADRB2 | 20.2 | 23.7 | 22.3 | 18.5 | 20.1 | 20.0 | 1.8 | Gs |
| 44 | GPR30 | 20.5 | 23.2 | 19.2 | 21.5 | 19.1 | 20.1 | 1.5 | GiA3o |
| 45 | F2RL2 | 20.7 | 19.2 | 20.8 | 21.4 | 19.6 | 20.1 | 0.8 | Unknown |
| 46 | PTGER2 | 20.2 | 20.6 | 20.2 | 20.6 | 19.3 | 20.1 | 0.5 | Gs |
| 47 | ADORA1 | 20.8 | 20.3 | 20.5 | 20.3 | 19.4 | 20.2 | 0.5 | Gi/Go |
| 48 | BAI2 | 19.5 | 20.7 | 20.6 | 20.4 | 20.2 | 20.2 | 0.4 | Unknown |
| 49 | PTGFR | 22.4 | 23.0 | 20.0 | 19.7 | 19.3 | 20.2 | 1.5 | Gq/G11 |
| 50 | EDG8 | 21.2 | 21.1 | 21.1 | 20.1 | 19.5 | 20.4 | 0.7 | Gi/Go, G12/G13 |
| 51 | GPR135 | 20.1 | 20.6 | 20.9 | 20.7 | 20.9 | 20.6 | 0.3 | Unknown |
| 52 | GPRC5B | 20.5 | 23.0 | 19.4 | 21.0 | 22.4 | 20.7 | 1.3 | Unknown |
| 53 | ADORA2B | 20.2 | 22.9 | 20.2 | 21.0 | 21.0 | 20.8 | 1.0 | Gs |
| 54 | GPR115 | 22.2 | 23.4 | 20.2 | 21.9 | 19.6 | 20.9 | 1.4 | Unknown |
| 55 | GPR63 | 21.0 | 21.4 | 23.8 | 19.6 | 21.2 | 20.9 | 1.4 | Unknown |
| 56 | GPR85 | 21.3 | 22.9 | 20.4 | 20.5 | 20.5 | 20.9 | 0.9 | Unknown |
| 57 | EBI2 | 20.8 | 21.7 | 22.9 | 20.0 | 20.8 | 20.9 | 1.0 | Gi/Go |
| 58 | P2RY11 | 21.0 | 21.3 | 20.7 | 21.3 | 21.2 | 21.1 | 0.2 | Gq/G11 |
| 59 | GPR150 | 21.7 | 23.3 | 22.2 | 20.6 | 20.2 | 21.2 | 1.1 | Unknown |
| 60 | MC1R | 21.9 | 23.2 | 21.7 | 21.1 | 21.1 | 21.6 | 0.8 | Gs |
| 61 | GPR75 | 21.6 | 22.5 | 22.3 | 21.1 | 21.6 | 21.7 | 0.5 | Gq/G11 |
| 62 | GPR39 | 21.4 | 23.8 | 21.5 | 21.2 | 21.8 | 21.7 | 0.9 | Gq/G11 |
| 63 | PTGER1 | 23.6 | 20.4 | 21.8 | 22.4 | 22.8 | 21.8 | 1.1 | Gq/G11 |
| 64 | ADORA2A | 22.2 | 23.5 | 22.8 | 21.8 | 20.9 | 22.0 | 0.9 | Gs |
| 65 | CALCRL | 23.5 | 21.8 | 21.5 | 22.2 | 22.2 | 22.1 | 0.7 | Gs |
| 66 | P2RY5 | 22.2 | 22.2 | 22.0 | 21.7 | 23.0 | 22.1 | 0.4 | Gs, Gi/Go, G12/G13 |
| 67 | GPR146 | 21.3 | 22.9 | 22.3 | 22.9 | 22.8 | 22.3 | 0.6 | Unknown |
| 68 | TM7SF1 | 21.9 | 22.9 | 21.9 | 22.4 | 23.0 | 22.3 | 0.5 | Unknown |
| 69 | PTGER3 | 22.8 | 23.8 | 23.0 | 21.5 | 22.8 | 22.6 | 0.7 | Gi/Go |
| 70 | GPR52 | 22.6 | 22.8 | 23.2 | 22.2 | 22.8 | 22.7 | 0.3 | Unknown |
| 71 | GPR21 | 22.8 | 23.2 | 23.3 | 22.2 | 22.5 | 22.7 | 0.4 | Gq/G11 |
| 72 | GPR22 | 22.4 | 23.3 | 22.7 | 23.2 | 22.4 | 22.8 | 0.4 | Gi/Go |
| 73 | ADRA2A | 23.8 | 23.7 | 22.7 | 21.9 | 23.1 | 22.9 | 0.7 | Gi/Go |
| 74 | GRPR | 21.8 | 24.6 | 23.5 | 22.9 | 23.1 | 22.9 | 0.9 | Gq/G11 |
| 75 | GPR160 | 21.8 | 24.7 | 23.8 | 22.7 | 23.4 | 22.9 | 1.0 | Unknown |
| 76 | PTGER4 | 22.9 | 23.7 | 22.5 | 25.3 | 22.7 | 22.9 | 0.4 | Gs |
| 77 | GPR3 | 22.7 | 24.8 | 23.5 | 22.5 | 22.5 | 23.0 | 0.9 | Gs |
| 78 | C5R1 | 23.4 | 22.6 | 24.8 | 23.7 | 23.0 | 23.3 | 0.7 | Gi/Go |
| 79 | LTB4R2 | 23.2 | 23.4 | 23.8 | 24.2 | 23.1 | 23.5 | 0.4 | Gi/Go |
| 80 | GPR34 | 24.7 | 24.9 | 24.3 | 23.6 | 22.1 | 23.5 | 1.0 | Gi/Go |
| 81 | GPR82 | 23.2 | 23.3 | 23.9 | 24.1 | 23.5 | 23.5 | 0.4 | Unknown |
| 82 | CELSR3 | 24.8 | 25.0 | 24.4 | 23.3 | 22.9 | 23.8 | 0.8 | Unknown |

TABLE 3

Comparison of the 82 commonly detected by GPCRs expressed by CAFs with their expression by PSCs

|  |  | GPCRs | Avg. ΔCt in CAFs | ΔCt in PSC | Fold Changes | | | | | Avg. Fold Change |
|---|---|---|---|---|---|---|---|---|---|---|
|  |  |  |  |  | CAF1 vs. PSC | CAF2 vs. PSC | CAF4 vs. PSC | CAF4 vs. PSC | CAF5 vs. PSC |  |
| Up-regulated | 1 | OXTR | 15.6 | 23.7 | 790.2 | 128.0 | 35.2 | 284.2 | 113.6 | 270.2 |
|  | 2 | GPR68 | 17.5 | 23.3 | 20.3 | 18.5 | 68.8 | 55.4 | 118.4 | 56.3 |
|  | 3 | GPR56 | 18.7 | 24.2 | 2.6 | 1.7 | 69.2 | 4.1 | 150.9 | 45.7 |
|  | 4 | GPRC5A | 15.2 | 20.6 | 59.8 | 4.9 | 49.7 | 71.7 | 33.8 | 44.0 |
|  | 5 | SSTR1 | 17.2 | 22.6 | 29.4 | 9.4 | 27.9 | 66.8 | 76.1 | 41.9 |
|  | 6 | BDKRB1 | 16.6 | 21.0 | 3.1 | 13.0 | 13.1 | 25.8 | 50.5 | 21.1 |
|  | 7 | PPYR1 | 19.7 | 23.9 | 8.3 | 60.4 | 4.1 | 4.9 | 17.1 | 18.9 |
|  | 8 | GPR37 | 18.7 | 22.7 | 4.5 | 30.9 | 0.7 | 43.3 | 1.6 | 16.2 |
|  | 9 | BDKRB2 | 18.5 | 22.5 | 1.2 | 10.4 | 11.8 | 20.6 | 32.2 | 15.2 |
|  | 10 | ADRB2 | 20.0 | 23.7 | 11.2 | 1.0 | 2.7 | 38.4 | 12.7 | 13.2 |
|  | 11 | F2R | 13.3 | 17.0 | 9.4 | 4.6 | 11.1 | 17.3 | 21.7 | 12.8 |
|  | 12 | GPR150 | 21.2 | 24.8 | 8.2 | 2.8 | 5.8 | 17.4 | 23.2 | 11.5 |
|  | 13 | GPR126 | 18.5 | 21.9 | 11.1 | 5.0 | 9.7 | 15.3 | 11.6 | 10.5 |
|  | 14 | GPR115 | 20.9 | 24.3 | 4.1 | 1.9 | 16.9 | 5.1 | 24.5 | 10.5 |
|  | 15 | FZD8 | 18.0 | 21.2 | 3.6 | 4.7 | 15.4 | 7.0 | 15.7 | 9.3 |
|  | 16 | BAI2 | 20.2 | 23.4 | 15.2 | 6.5 | 6.7 | 8.0 | 9.3 | 9.1 |
|  | 17 | FZD1 | 16.2 | 19.3 | 4.4 | 2.7 | 13.6 | 8.3 | 16.0 | 9.0 |
|  | 18 | GPR176 | 14.9 | 18.0 | 12.0 | 4.7 | 6.1 | 13.3 | 6.4 | 8.5 |
|  | 19 | TBXA2R | 19.2 | 22.2 | 8.4 | 4.0 | 5.2 | 9.3 | 13.1 | 8.0 |
|  | 20 | F2RL2 | 20.1 | 23.1 | 5.3 | 14.6 | 4.9 | 3.4 | 11.7 | 8.0 |
|  | 21 | F2RL1 | 16.4 | 19.1 | 0.7 | 0.3 | 6.8 | 1.7 | 23.0 | 6.5 |
|  | 22 | GPR146 | 22.3 | 24.9 | 12.3 | 4.1 | 6.2 | 4.0 | 4.2 | 6.1 |
|  | 23 | ELTD1 | 17.2 | 19.8 | 7.0 | 1.5 | 5.8 | 4.6 | 11.6 | 6.1 |
|  | 24 | LPHN2 | 15.3 | 17.7 | 2.6 | 1.4 | 9.8 | 3.5 | 9.0 | 5.3 |
|  | 25 | FZD4 | 16.8 | 19.1 | 5.5 | 2.4 | 5.2 | 7.0 | 4.5 | 4.9 |
|  | 26 | C11ORF4 | 16.8 | 19.0 | 3.7 | 1.8 | 3.2 | 6.3 | 7.6 | 4.5 |
|  | 27 | CD97 | 16.7 | 18.8 | 4.7 | 3.9 | 2.6 | 4.1 | 5.7 | 4.2 |
|  | 28 | GPR16.1 | 19.3 | 21.3 | 3.3 | 3.4 | 2.5 | 5.0 | 6.0 | 4.0 |
|  | 29 | FZD2 | 17.3 | 19.2 | 4.8 | 4.9 | 3.4 | 3.6 | 2.7 | 3.9 |
|  | 30 | PTGIR | 17.4 | 19.3 | 3.9 | 1.2 | 0.9 | 8.6 | 3.7 | 3.7 |
|  | 31 | EBI2 | 20.9 | 22.8 | 4.0 | 2.2 | 0.9 | 7.0 | 4.0 | 3.6 |
|  | 32 | GPR153 | 18.5 | 20.3 | 5.1 | 2.8 | 2.4 | 5.3 | 2.1 | 3.5 |
|  | 33 | GPR125 | 18.4 | 20.2 | 2.6 | 1.7 | 3.5 | 3.3 | 6.4 | 3.5 |
|  | 34 | GPR21 | 22.7 | 24.3 | 3.0 | 2.3 | 2.1 | 4.5 | 3.7 | 3.1 |
|  | 35 | GRPR | 22.9 | 24.5 | 6.4 | 0.9 | 2.0 | 3.1 | 2.7 | 3.0 |
|  | 36 | ADORA2A | 22.0 | 23.6 | 2.6 | 1.0 | 1.7 | 3.5 | 6.2 | 3.0 |
|  | 37 | GPR52 | 22.7 | 24.1 | 2.7 | 2.5 | 1.8 | 3.8 | 2.5 | 2.7 |
|  | 38 | GPR22 | 22.8 | 24.0 | 3.2 | 1.6 | 2.5 | 1.8 | 3.1 | 2.4 |
|  | 39 | LGR4 | 18.0 | 19.1 | 1.0 | 0.7 | 5.6 | 1.4 | 2.1 | 2.1 |
| Unchanged | 1 | GPR39 | 21.7 | 22.7 | 2.4 | 0.5 | 2.4 | 2.8 | 1.9 | 2.0 |
|  | 2 | GPR82 | 23.5 | 24.4 | 2.3 | 2.2 | 1.4 | 1.2 | 1.9 | 1.8 |
|  | 3 | FZD7 | 18.6 | 19.5 | 3.1 | 2.2 | 2.9 | 0.4 | 0.5 | 1.8 |
|  | 4 | GPR135 | 20.6 | 21.5 | 2.6 | 1.8 | 1.5 | 1.7 | 1.5 | 1.8 |
|  | 5 | MRGPRF | 18.5 | 19.3 | 1.4 | 2.2 | 1.9 | 1.0 | 1.9 | 1.7 |
|  | 6 | PTGER3 | 22.6 | 23.3 | 1.5 | 0.7 | 1.2 | 3.5 | 1.5 | 1.7 |
|  | 7 | EDG3 | 19.6 | 20.2 | 1.9 | 1.3 | 1.5 | 1.7 | 1.1 | 1.5 |
|  | 8 | LTB4R2 | 23.5 | 24.0 | 1.7 | 1.5 | 1.1 | 0.9 | 1.9 | 1.4 |
|  | 9 | GPR75 | 21.7 | 22.2 | 1.5 | 0.8 | 0.9 | 2.1 | 1.6 | 1.4 |
|  | 10 | EDG2 | 15.8 | 16.2 | 1.2 | 0.7 | 0.9 | 2.3 | 1.5 | 1.3 |
|  | 11 | MC1R | 21.6 | 22.0 | 1.0 | 0.4 | 1.2 | 1.8 | 1.8 | 1.3 |
|  | 12 | SMO | 19.1 | 19.4 | 1.8 | 0.3 | 1.5 | 0.9 | 1.3 | 1.2 |
|  | 13 | GABBR1 | 18.0 | 18.1 | 0.8 | 0.8 | 0.7 | 1.7 | 1.5 | 1.1 |
|  | 14 | OPN3 | 18.8 | 18.7 | 1.0 | 1.2 | 0.2 | 2.0 | 0.7 | 1.0 |
|  | 15 | EDNRA | 17.3 | 17.3 | 0.3 | 0.4 | 0.7 | 0.9 | 2.7 | 1.0 |
|  | 16 | GPR124 | 16.3 | 16.2 | 0.8 | 2.0 | 0.4 | 1.0 | 0.6 | 0.9 |
|  | 17 | GPR173 | 19.5 | 19.4 | 1.1 | 0.5 | 0.9 | 0.7 | 1.5 | 0.9 |
|  | 18 | PTGER4 | 23.0 | 22.9 | 1.0 | 0.6 | 1.3 | 0.7 | 1.1 | 0.9 |
|  | 19 | PZRY11 | 21.1 | 20.8 | 0.9 | 0.7 | 1.1 | 0.7 | 0.8 | 0.8 |
|  | 20 | P2RY5 | 22.1 | 21.8 | 0.8 | 0.8 | 0.9 | 1.1 | 0.4 | 0.8 |
|  | 21 | CELSR3 | 23.8 | 23.4 | 0.4 | 0.3 | 0.5 | 1.1 | 1.5 | 0.8 |
|  | 22 | GPRC5B | 20.7 | 20.3 | 0.9 | 0.2 | 1.9 | 0.6 | 0.2 | 0.8 |
|  | 23 | CHRM2 | 16.8 | 16.4 | 0.5 | 0.9 | 0.0 | 2.0 | 0.2 | 0.7 |
|  | 24 | FZD6 | 15.8 | 15.1 | 0.7 | 0.4 | 0.3 | 1.3 | 0.5 | 0.6 |
|  | 25 | GPR85 | 20.9 | 20.2 | 0.5 | 0.2 | 0.8 | 0.8 | 0.8 | 0.6 |
| Down-regulated | 1 | GPR51 | 19.4 | 18.0 | 0.0 | 0.1 | 0.1 | 0.7 | 1.1 | 0.4 |
|  | 2 | PTGFR | 20.2 | 18.8 | 0.1 | 0.1 | 0.5 | 0.6 | 0.7 | 0.4 |
|  | 3 | EDNRB | 17.4 | 15.9 | 0.0 | 0.2 | 0.0 | 1.3 | 0.3 | 0.4 |
|  | 4 | ADORA2B | 20.8 | 19.2 | 0.5 | 0.1 | 0.5 | 0.3 | 0.3 | 0.3 |
|  | 5 | EDG1 | 19.5 | 17.9 | 0.2 | 0.1 | 0.1 | 0.1 | 1.1 | 0.3 |
|  | 6 | PTGER1 | 21.8 | 19.7 | 0.1 | 0.6 | 0.2 | 0.1 | 0.1 | 02 |
|  | 7 | GPR63 | 20.9 | 18.3 | 0.1 | 0.1 | 0.0 | 0.4 | 0.1 | 02 |

TABLE 3-continued

Comparison of the 82 commonly detected by GPCRs expressed by CAFs with their expression by PSCs

|  |  | GPCRs | Avg. ΔCt in CAFs | ΔCt in PSC | Fold Changes | | | | | Avg. Fold Change |
|---|---|---|---|---|---|---|---|---|---|---|
|  |  |  |  |  | CAF1 vs. PSC | CAF2 vs. PSC | CAF4 vs. PSC | CAF4 vs. PSC | CAF5 vs. PSC |  |
|  | 8 | CALCRL | 22.1 | 19.5 | 0.1 | 0.2 | 0.2 | 0.2 | 0.2 | 0.2 |
|  | 9 | FTGER2 | 20.1 | 17.4 | 0.1 | 0.1 | 0.1 | 0.1 | 0.3 | 0.1 |
| Uniquely expressed | 1 | ADRA2A | 22.9 | ND |  |  |  |  |  |  |
|  | 2 | GPR30 | 20.1 | ND |  |  |  |  |  |  |
|  | 3 | ADORA1 | 20.2 | ND |  |  |  |  |  |  |
|  | 4 | EDG8 | 20.4 | ND |  |  |  |  |  |  |
|  | 5 | TM7SF1 | 22.3 | ND |  |  |  |  |  |  |
|  | 6 | GPR160 | 22.9 | ND |  |  |  |  |  |  |
|  | 7 | C5R1 | 23.3 | ND |  |  |  |  |  |  |
|  | 8 | GPR34 | 23.5 | ND |  |  |  |  |  |  |
|  | 9 | GPR3 | 23.0 | ND |  |  |  |  |  |  |

TABLE 4

Comparison of the 82 commonly detected by GPCRs expressed by CAFs with their expression by PFs

|  |  | GPCRs | Avg. ΔCT in CAFs | ΔCt in PFs | Fold change | | | | | Avg. Fold Change |
|---|---|---|---|---|---|---|---|---|---|---|
|  |  |  |  |  | CAF1 vs. PF | CAF2 vs. PF | CAF3 vs. PF | CAF4 vs. PF | CAF5 vs. PF |  |
| Up-regulated | 1 | GPR56 | 18.7 | 24.6 | 3.5 | 2.2 | 91.6 | 5.4 | 199.7 | 60.5 |
|  | 2 | GPR68 | 17.5 | 21.8 | 7.0 | 6.4 | 23.8 | 19.1 | 40.9 | 19.4 |
|  | 3 | F2RL1 | 16.4 | 20.5 | 1.9 | 0.8 | 17.4 | 4.4 | 59.0 | 16.7 |
|  | 4 | EDG-1 | 19.5 | 23.5 | 12.2 | 5.8 | 4.3 | 3.9 | 54.4 | 16.1 |
|  | 5 | SSTR1 | 17.2 | 21.1 | 10.3 | 3.3 | 9.7 | 23.3 | 26.5 | 14.6 |
|  | 6 | GPRC5A | 15.2 | 19.0 | 19.5 | 1.6 | 16.2 | 23.4 | 11.1 | 14.4 |
|  | 7 | GPR51 | 19.4 | 22.9 | 0.8 | 3.6 | 1.8 | 19.8 | 31.9 | 11.6 |
|  | 8 | FZD4 | 16.8 | 20.3 | 12.4 | 5.5 | 11.7 | 16.0 | 10.2 | 11.2 |
|  | 9 | GPR150 | 21.2 | 24.7 | 7.8 | 2.7 | 5.5 | 16.6 | 22.1 | 11.0 |
|  | 10 | F2RL2 | 20.1 | 23.5 | 6.9 | 18.9 | 6.4 | 4.4 | 15.2 | 10.4 |
|  | 11 | FZD8 | 18.0 | 21.0 | 3.1 | 4.1 | 13.3 | 6.1 | 13.6 | 8.0 |
|  | 12 | F2R | 13.3 | 15.9 | 4.3 | 2.1 | 5.1 | 7.9 | 9.9 | 5.9 |
|  | 13 | OXTR | 15.6 | 17.9 | 14.6 | 2.4 | 0.7 | 5.2 | 2.1 | 5.0 |
|  | 14 | LPHN2 | 15.3 | 17.6 | 2.4 | 1.3 | 9.1 | 3.2 | 8.3 | 4.9 |
|  | 15 | GPR21 | 22.7 | 25.0 | 4.6 | 3.5 | 3.2 | 7.0 | 5.7 | 4.8 |
|  | 16 | EDG8 | 20.4 | 22.4 | 2.4 | 2.5 | 2.4 | 4.9 | 7.6 | 4.0 |
|  | 17 | MRGPRF | 18.5 | 20.4 | 3.0 | 4.6 | 4.1 | 2.2 | 4.1 | 3.6 |
|  | 18 | GPR126 | 18.5 | 20.3 | 3.8 | 1.7 | 3.3 | 5.2 | 3.9 | 3.6 |
|  | 19 | GPR75 | 21.7 | 23.5 | 3.8 | 2.0 | 2.3 | 5.2 | 3.8 | 3.4 |
|  | 20 | SMO | 19.1 | 20.9 | 5.3 | 1.0 | 4.4 | 2.5 | 3.7 | 3.4 |
|  | 21 | GPR153 | 18.5 | 20.2 | 4.6 | 2.5 | 4.8 | 1.9 | 3.2 | 3.2 |
|  | 22 | GPR22 | 22.8 | 24.4 | 4.0 | 2.1 | 3.1 | 2.3 | 3.9 | 3.1 |
|  | 23 | GPR3 | 23.0 | 24.6 | 3.7 | 0.9 | 2.2 | 4.2 | 4.2 | 3.1 |
|  | 24 | CALCRL | 22.1 | 23.6 | 1.1 | 3.7 | 4.4 | 2.7 | 2.7 | 2.9 |
|  | 25 | P2RY5 | 22.1 | 23.7 | 2.8 | 2.8 | 3.2 | 3.9 | 1.6 | 2.9 |
|  | 26 | LGR4 | 18.0 | 19.5 | 1.3 | 0.9 | 7.3 | 1.8 | 2.8 | 2.8 |
|  | 27 | GPR63 | 20.9 | 22.3 | 2.5 | 1.9 | 0.4 | 6.8 | 2.2 | 2.7 |
|  | 28 | ADORA2A | 22.0 | 23.4 | 2.3 | 0.9 | 1.5 | 3.1 | 5.5 | 2.7 |
|  | 29 | GPR124 | 16.3 | 17.7 | 2.2 | 5.4 | 1.1 | 2.9 | 1.6 | 2.6 |
|  | 30 | EBI2 | 20.9 | 22.3 | 2.9 | 1.6 | 0.7 | 5.0 | 2.9 | 2.6 |
|  | 31 | C11ORF4 | 16.8 | 18.2 | 2.1 | 1.0 | 1.8 | 3.6 | 4.3 | 2.6 |
|  | 32 | FZD1 | 16.2 | 17.5 | 1.2 | 0.7 | 3.7 | 2.3 | 4.4 | 2.5 |
|  | 33 | CD97 | 16.7 | 17.9 | 2.6 | 2.1 | 1.5 | 2.3 | 3.2 | 2.3 |
|  | 34 | MC1R | 21.6 | 22.8 | 1.9 | 0.8 | 2.1 | 3.3 | 3.2 | 2.2 |
|  | 35 | BAI2 | 20.2 | 21.3 | 3.6 | 1.5 | 1.6 | 1.9 | 2.2 | 2.2 |
|  | 36 | GPR176 | 14.9 | 16.0 | 3.0 | 1.2 | 1.5 | 3.4 | 1.6 | 2.1 |
|  | 37 | ELTD1 | 17.2 | 18.2 | 2.4 | 0.5 | 2.0 | 1.5 | 3.9 | 2.1 |
| Unchanged | 1 | FZD2 | 17.3 | 18.3 | 2.5 | 2.6 | 1.8 | 1.9 | 1.4 | 2.0 |
|  | 2 | GPR125 | 18.4 | 19.4 | 1.5 | 1.0 | 2.0 | 1.9 | 3.7 | 2.0 |
|  | 3 | GPR30 | 20.1 | 21.1 | 1.5 | 0.2 | 3.7 | 0.8 | 3.8 | 2.0 |
|  | 4 | GPR135 | 20.6 | 21.6 | 2.8 | 2.0 | 1.6 | 1.8 | 1.6 | 2.0 |
|  | 5 | GPR52 | 22.7 | 23.6 | 2.0 | 1.8 | 1.3 | 2.7 | 1.8 | 1.9 |
|  | 6 | PTGIR | 17.4 | 18.4 | 2.0 | 0.6 | 0.5 | 4.5 | 1.9 | 1.9 |
|  | 7 | EDG2 | 15.8 | 16.7 | 1.7 | 1.0 | 1.3 | 3.2 | 2.1 | 1.8 |
|  | 8 | GABBR1 | 18.0 | 18.8 | 1.4 | 1.2 | 1.1 | 2.7 | 2.4 | 1.8 |
|  | 9 | PTGFR | 20.2 | 21.0 | 0.4 | 0.3 | 2.0 | 2.5 | 3.3 | 1.7 |

TABLE 4-continued

Comparison of the 82 commonly detected by GPCRs expressed by CAFs with their expression by PFs

| | | GPCRs | Avg. ΔCT in CAFs | ΔCt in PFs | Fold change CAF1 vs. PF | CAF2 vs. PF | CAF3 vs. PF | CAF4 vs. PF | CAF5 vs. PF | Avg. Fold Change |
|---|---|---|---|---|---|---|---|---|---|---|
| | 10 | EDNRA | 17.3 | 18.0 | 0.5 | 0.7 | 1.1 | 1.4 | 4.4 | 1.6 |
| | 11 | GPR85 | 20.9 | 21.6 | 1.2 | 0.4 | 2.2 | 2.1 | 2.1 | 1.6 |
| | 12 | FZD7 | 18.6 | 19.3 | 2.7 | 2.0 | 2.6 | 0.4 | 0.4 | 1.6 |
| | 13 | GPR173 | 19.5 | 20.1 | 1.8 | 0.8 | 1.5 | 1.2 | 2.5 | 1.5 |
| | 14 | GPR161 | 19.3 | 19.7 | 1.1 | 1.2 | 0.9 | 1.7 | 2.0 | 1.4 |
| | 15 | GPR160 | 22.9 | 23.3 | 2.9 | 0.4 | 0.7 | 1.5 | 0.9 | 1.3 |
| | 16 | LTB4R2 | 23.5 | 23.8 | 1.5 | 1.3 | 1.0 | 0.8 | 1.7 | 1.3 |
| | 17 | TBXA2R | 19.2 | 19.5 | 1.3 | 0.6 | 0.8 | 1.5 | 2.0 | 1.3 |
| | 18 | TM7SF1 | 22.3 | 22.6 | 1.6 | 0.8 | 1.7 | 1.1 | 0.8 | 1.2 |
| | 19 | EDG3 | 19.6 | 19.6 | 1.3 | 0.9 | 1.0 | 1.2 | 0.7 | 1.0 |
| | 20 | FZD6 | 15.8 | 15.8 | 1.1 | 0.7 | 0.5 | 2.0 | 0.8 | 1.0 |
| | 21 | PTGER1 | 21.8 | 21.7 | 0.3 | 2.4 | 0.9 | 0.6 | 0.5 | 0.9 |
| | 22 | GPR39 | 21.7 | 21.5 | 1.1 | 0.2 | 1.0 | 1.2 | 0.8 | 0.9 |
| | 23 | OPN3 | 18.8 | 18.4 | 0.8 | 0.9 | 0.1 | 1.5 | 0.5 | 0.8 |
| | 24 | P2RY11 | 21.1 | 20.4 | 0.6 | 0.5 | 0.8 | 0.5 | 0.6 | 0.6 |
| | 25 | PTGER2 | 20.1 | 19.3 | 0.5 | 0.4 | 0.5 | 0.4 | 0.9 | 0.5 |
| | 26 | GPR146 | 22.3 | 21.3 | 1.0 | 0.3 | 0.5 | 0.3 | 0.3 | 0.5 |
| Down-regulated | 1 | PTGER4 | 23.0 | 21.6 | 0.4 | 0.2 | 0.5 | 0.3 | 0.5 | 0.4 |
| | 2 | ADORA2B | 20.8 | 19.2 | 0.5 | 0.1 | 0.5 | 0.3 | 0.3 | 0.3 |
| | 3 | ADRB2 | 20.0 | 18.2 | 0.2 | 0.0 | 0.1 | 0.8 | 0.3 | 0.3 |
| Uniquely expressed | 1 | BDKRB2 | 18.5 | ND | | | | | | |
| | 2 | GPRC5B | 20.7 | ND | | | | | | |
| | 3 | GPR115 | 20.9 | ND | | | | | | |
| | 4 | BDKRB1 | 16.6 | ND | | | | | | |
| | 5 | CHRM2 | 16.8 | ND | | | | | | |
| | 6 | EDNRB | 17.4 | ND | | | | | | |
| | 7 | ADRA2A | 22.9 | ND | | | | | | |
| | 8 | ADORA1 | 20.2 | ND | | | | | | |
| | 9 | GPR37 | 18.7 | ND | | | | | | |
| | 10 | PTGER3 | 22.6 | ND | | | | | | |
| | 11 | PPYR1 | 19.7 | ND | | | | | | |
| | 12 | GRPR | 22.9 | ND | | | | | | |
| | 13 | C5R1 | 23.3 | ND | | | | | | |
| | 14 | GPR34 | 23.5 | ND | | | | | | |
| | 15 | GPR82 | 23.5 | ND | | | | | | |
| | 16 | CELSR3 | 23.8 | ND | | | | | | |

TABLE 5

Tumor types (and their abbreviations) assessed and numbers of replicates

| Number | Cancer Type | Histology/Subtype | Number of Replicates |
|---|---|---|---|
| 1 | Adrenocortical Cancer (ACC) | Adrenocortical carcinoma - Usual Type | 73 |
| 2 | Bladder Cancer (BLCA) | Papillary bladder cancer (BLCA Pap) | 130 |
| | | Non-papillary bladder cancer (BLCA NonPap) | 267 |
| 3 | Breast Cancer (BRCA) | Infiltrating ductal carcinoma (IDC), Her2 positive (BRCA_1DC_Her2+] | 48 |
| | | IDC, ER positive (BRCA_IDC_ER+) | 431 |
| | | IDC, Triple positive (BRCA_IDC_3pl+) | 54 |
| | | IDC, Triple negative (BRCA_IDC_3pl−) | 109 |
| 4 | Cervical Cancer (CESC) | Invasive Lobular Carcinoma (ILC), ER positive (BRCA_Lob_ER+) | 57 |
| | | Cervical Squamous Cell Carcinoma (CESC_CervSq) | 252 |
| | | Endocervical Adenocarcinoma of the Usual Type (CESC_ECAD) | 21 |
| | | Mucinous Adenocarcinoma of Endocervical Type (CESC_Muc) | 17 |
| 5 | Colon Cancer (COAD) | Colon Adenocarcinoma in the sigmoid colon (COAD_Sig) | 71 |
| | | Colon Adenocarcinoma in the transverse colon (COAD_Trans) | 22 |
| 6 | Esophageal Cancer (ESCA) | Esophagus Adenocarcinoma (ESCA AD) | 89 |
| | | Esophagus Squamous Cell Carcinoma (ESCA SQC] | 92 |
| 7 | Kidney Papillary Cell Carcinoma (KIRP) | — | 288 |
| 8 | Kidney Clear Cell Carcinoma (KIRC) | — | 523 |
| 9 | Kidney Chromophobe (KICH) | — | 66 |
| 10 | Liver Cancer (LIHC) | Liver Hepatocellular Carcinoma (LIHC) | 360 |
| 11 | Lung adenocarcinoma (LUAD) | Lung Papillary Adenocarcinoma (LUAD_Pap) | 23 |
| | | Lung Bronchioloalveolar Carcinoma Non-Mucinous (LUAD_BCNM) | 19 |
| | | Lung Adenocarcinoma-Not Otherwise Specified (LUAO_NOS) | 308 |
| | | Lung Adenocarcinoma-Mixed (LUAD_Mixed) | 105 |
| | | Lung Acinar Adenocarcinoma (LUAD_Acinar) | 18 |

TABLE 5-continued

Tumor types (and their abbreviations) assessed and numbers of replicates

| Number | Cancer Type | Histology/Subtype | Number of Replicates |
|---|---|---|---|
| 12 | Lung squamous cell carcinoma (LSQC) | Lung Squamous Cell Carcinoma- Not Otherwise Specified (LSQC_NOS) | 468 |
|  |  | Lung Basaloid Squamous Cell Carcinoma (LSQC Basal) | 14 |
| 13 | Skin Cutaneous Melanoma (SKCM) | Primary melanomas (SKCM_Primary) | 100 |
|  |  | Distant metastases (SKCM_DMet) | 68 |
| 14 | Ovarian Cancer (OV) | Ovarian Serous Cystadenocarcinoma (OV) | 418 |
| IS | Pancreatic Cancer (PAAD) | Pancreatic Ductal Adenocarcinoma (PDAC) | 147 |
| 16 | Prostate Cancer (PRAD) | Prostate Adenocarcinoma Acinar Type (PRAD) | 475 |
| 17 | Stomach Cancer (STAD) | Stomach, Adenocarcinoma, Diffuse Type (STAD_Diff) | 68 |
|  |  | Stomach, Adenocarcinoma, Not Otherwise Specified (STAD_NOS) | 154 |
|  |  | Stomach, Intestinal Adenocarcinoma, Mucinous Type (STAD_Muc) | 19 |
|  |  | Stomach, Intestinal Adenocarcinoma, Not Otherwise Specified (STAD_IntNOS) | 73 |
|  |  | Stomach, Intestinal Adenocarcinoma, Tubular Type (STAD_IntTub) | 76 |
|  |  | Stomach Adenocarcinoma, Signet Ring Type (STAD_Sig) | 12 |
| 18 | Testicular Cancer (TGCT) | Seminoma (TGCT_Sem) | 72 |
|  |  | Non-seminoma (TGCT_NonSem) | 65 |
| 19 | Thyroid Cancer (THCA) | Thyroid Papillary Carcinoma - Classical/usual (THCA Usual) | 3S8 |
|  |  | Thyroid Papillary Carcinoma - Follicular (>=99% follicular patterned) (THCA_fol) | 101 |
|  |  | Thyroid Papillary Carcinoma - Tall Cell (>=50% tall cell features) (THCA_TC) | 36 |
| 20 | Uterine Carcinosarcoma (UCS) | Uterine Carcinosarcoma/Malignant Mixed Mullerian Tumor (MMMT): (UCS_NOS) | 24 |
|  |  | Uterine Carcinosarcoma/MMMT: Heterologous Type (UCS_Het) | 20 |
|  |  | Uterine Carcinosarcoma/MMMT: Homologous Type (UCS_Homo) | 13 |

Abbreviations

α-SMA alpha smooth muscle actin
CAFs cancer-associated fibroblasts
CM conditioned media
cAMP cyclic adenosine monophosphate
CREB cAMP response element binding protein
CPM counts per million
DE differential expression
FPKM fragments per kilobase of transcript per Million mapped reads
GIST gastrointestinal stromal tumor
GPCRs G protein-coupled receptors
GPR68 G protein-coupled receptor 68
IL6 interleukin-6
PDAC pancreatic ductal adenocarcinoma
PFs pancreatic fibroblasts
PKA protein kinase A
PSCs pancreatic stellate cells
TGFβ1 Transforming growth factor beta 1
TNFα tumor necrosis factor alpha

REFERENCES

1. American Cancer Society. (2017) Cancer Facts & Figures 2017. 1-71
2. Rahib, L., Smith, B. D., Aizenberg, R., Rosenzweig, A. B., Fleshman, J. M., and Matrisian, L. M. (2014) Projecting cancer incidence and deaths to 2030: The unexpected burden of thyroid, liver, and pancreas cancers in the united states. Cancer Res. 74, 2913-2921
3. Siegel, R. L., Miller, K. D., and Jemal, A. (2017) Cancer Statistics, 2017. 67, 7-30
4. Ryan, D. P., Hong, T. S., and Bardeesy, N. (2014) Pancreatic Adenocarcinoma. N. Engl. J. Med. 371, 1039-1049
5. Kleger, A., Perkhofer, L., and Seufferlein, T. (2014) Smarter drugs emerging in pancreatic cancer therapy. Ann. Oncol. 25, 1260-1270
6. Erkan, M., Michalski, C. W., Rieder, S., Reiser-Erkan, C., Abiatari, I., Kolb, A., Giese, N. A., Esposito, I., Friess, H., and Kleeff, J. (2008) The Activated Stroma Index Is a Novel and Independent Prognostic Marker in Pancreatic Ductal Adenocarcinoma. Clin. Gastroenterol. Hepatol. 6, 1155-1161
7. Hezel, A. F., Kimmelman, A. C., Stanger, B. Z., Bardeesy, N., and Depinho, R. A. (2006) Genetics and biology of pancreatic ductal adenocarcinoma. Genes Dev. 1, 1218-1249
8. Neesse A, Michl P, Frese K K, Feig C, Cook N, Jacobetz M A, Lolkema M P, Buchholz M, Olive K P, Gress T M, T. D. (2011) Stromal biology and therapy in pancreatic cancer. Gut 60, 861-868
9. Erkan, M., Hausmann, S., Michalski, C. W., Fingerle, A. a., Dobritz, M., Kleeff, J., and Friess, H. (2012) The role of stroma in pancreatic cancer: diagnostic and therapeutic implications. Nat. Rev. Gastroenterol. Hepatol. 9, 454-467
10. Feig, C., Gopinathan, A., Neesse, A., Chan, D. S., Cook, N., and Tuveson, D. A. (2012) The pancreas cancer microenvironment. Clin. Cancer Res. 18, 4266-4276
11. Wehr, A., Furth, E., Sangar, V., Blair, I., and Yu, K. (2011) Analysis of the human pancreatic stellate cell secreted proteome. Pancreas 40, 557-566
12. Sherman, M. H., Yu, R. T., Engle, D. D., Ding, N., Atkins, A. R., Tiriac, H., Collisson, E. A., Connor, F., Van Dyke, T., Kozlov, S., Martin, P., Tseng, T. W., Dawson, D. W., Donahue, T. R., Masamune, A., Shimosegawa, T., Apte, M. V., Wilson, J. S., Ng, B., Lau, S. L., Gunton, J. E., Wahl, G. M., Hunter, T., Drebin, J. A., O'Dwyer, P. J., Liddle, C., Tuveson, D. A., Downes, M., and Evans, R. M. (2014) Vitamin D receptor-mediated stromal reprogramming suppresses pancreatitis and enhances pancreatic cancer therapy. Cell 159, 80-93
13. Roshani, R., McCarthy, F., and Hagemann, T. (2014) Inflammatory cytokines in human pancreatic cancer. Cancer Lett. 345, 157-163
14. Vassilatis, D. K., Hohmann, J. G., Zeng, H., Li, F., Ranchalis, J. E., Mortrud, M. T., Brown, A., Rodriguez, S. S., Weller, J. R., Wright, A. C., Bergmann, J. E., and Gaitanaris, G. a. (2003) The G protein-coupled receptor repertoires of human and mouse. Proc. Natl. Acad. Sci. U.S.A 100, 4903-4908

15. Pierce, K. L., Premont, R. T., and Lefkowitz, R. J. (2002) Signalling: Seven-transmembrane receptors. Nat. Rev. Mol. Cell Biol. 3, 639-650
16. Overington, J. P., Al-Lazikani, B., and Hopkins, A. L. (2006) How many drug targets are there? Nat. Rev. Drug Discov. 5, 993-996
17. Dorsam, R. T. and Gutkind, J. S. (2007) G-protein-coupled receptors and cancer. Nat. Rev. Cancer 7, 79-94
18. Lappano, R. and Maggiolini, M. (2011) G protein-coupled receptors: novel targets for drug discovery in cancer. Nat. Rev. Drug Discov. 10, 47-60
19. Snead, A. N. and Insel, P. A. (2012) Defining the cellular repertoire of GPCRs identifies a profibrotic role for the most highly expressed receptor, protease-activated receptor 1, in cardiac fibroblasts. FASEB J. 26, 4540-4547
20. Lu, D., Aroonsakool, N., Yokoyama, U., Patel, H. H., and Insel, P. A. (2013) Increase in cellular cyclic AMP concentrations reverses the profibrogenic phenotype of cardiac myofibroblasts: a novel therapeutic approach for cardiac fibrosis. Mol. Pharmacol. 84, 787-793
21. Dobin, A., Davis, C. A., Schlesinger, F., Drenkow, J., Zaleski, C., Jha, S., Batut, P., Chaisson, M., and Gingeras, T. R. (2013) STAR: Ultrafast universal RNA-seq aligner. Bioinformatics 29, 15-21
22. Roberts, A., Trapnell, C., Donaghey, J., Rinn, J. L., and Pachter, L. (2011) Improving RNA-Seq expression estimates by correcting for fragment bias. Genome Biol. 12, R22
23. Trapnell, C., Williams, B. a, Pertea, G., Mortazavi, A., Kwan, G., van Baren, M. J., Salzberg, S. L., Wold, B. J., and Pachter, L. (2011) Transcript assembly and abundance estimation from RNA-Seq reveals thousands of new transcripts and switching among isoforms. Nat. Biotechnol. 28, 511-515
24. Robinson, M. D., McCarthy, D. J., and Smyth, G. K. (2009) edgeR: A Bioconductor package for differential expression analysis of digital gene expression data. Bioinformatics 26, 139-140
25. Edgar, R., Domrachev, M., and Lash, A. E. (2002) Gene Expression Omnibus: NCBI gene expression and hybridization array data repository. Nucleic Acids Res. 30, 207-210
26. Bjarnadottir, T. K., Gloriam, D. E., Hellstrand, S. H., Kristiansson, H., Fredriksson, R., and Schioth, H. B. (2006) Comprehensive repertoire and phylogenetic analysis of the G protein-coupled receptors in human and mouse. Genomics 88, 263-273
27. Ludwig, M.-G., Vanek, M., Guerini, D., Gasser, J. A., Jones, C. E., Junker, U., Hofstetter, H., Wolf, R. M., and Seuwen, K. (2003) Proton-sensing G-protein-coupled receptord. Nature 425, 93-98
28. Damaghi, M., Wojtkowiak, J. W., and Gillies, R. J. (2013) pH sensing and regulation in cancer. Front. Physiol. 4, 1-10
29. Haqq, J., Howells, L. M., Garcea, G., Metcalfe, M. S., Steward, W. P., and Dennison, A. R. (2014) Pancreatic stellate cells and pancreas cancer: current perspectives and future strategies. Eur. J. Cancer 50, 2570-2582
30. Apte, M. V., Wilson, J. S., Lugea, A., and Pandol, S. J. (2013) A starring role for stellate cells in the pancreatic cancer microenvironment. Gastroenterology 144, 1210-1219
31. Apte, M. V, Haber, P. S., Darby, S. J., Rodgers, S. C., McCaughan, G. W., Korsten, M. A., Pirola, R. C., and Wilson, J. S. (1999) Pancreatic stellate cells are activated by proinflammatory cytokines: implications for pancreatic fibrogenesis. Gut 44, 534-541
32. Kordes, C., Brookmann, S., Haussinger, D., and Klonowski-Stumpe, H. (2005) Differential and synergistic effects of platelet-derived growth factor-BB and transforming growth factor-01 on activated pancreatic stellate cells. Pancreas 31, 156-167
33. de Valliere, C., Wang, Y., Eloranta, J. J., Vidal, S., Clay, I., Spalinger, M. R., Tcymbarevich, I., Terhalle, A., Ludwig, M.-G., Suply, T., Fried, M., Kullak-Ublick, G. A., Frey-Wagner, I., Scharl, M., Seuwen, K., Wagner, C. A., and Rogler, G. (2015) G Protein-coupled pH-sensing Receptor OGR1 Is a Regulator of Intestinal Inflammation. Inflamm. Bowel Dis. 21, 1269-1281
34. Valliere, C. De, Cosin-roger, J., Simmen, S., Atrott, K., Melhem, H., Zeitz, J., Madanchi, M., Tcymbarevich, I., Fried, M., Kullak-ublick, G. A., Vavricka, S. R., Misselwitz, B., Seuwen, K., Wagner, C. A., Eloranta, J. J., Rogler, G., and Ruiz, P. A. (2016) Hypoxia Positively Regulates the Expression of pH-Sensing. Cell. Mol. Gastroenterol. Hepatol. 2, 796-810
35. Gillies, R. J. and Bhujwalla, Z. (1994) 31P-MRS measurements of extracellular pH of tumors using 3-aminopropylphosphonate. Am. J. Physiol. 267, C195-203
36. Sluis, R. Van, Bhujwalla, Z. M., Raghunand, N., and Ballesteros, P. (1999) In Vivo Imaging of Extracellular pH Using 1H MRSI. Magn. Reson. Med. 41, 743-750
37. Huang, X.-P., Karpiak, J., Kroeze, W. K., Zhu, H., Chen, X., Moy, S. S., Saddoris, K. A., Nikolova, V. D., Farrell, M. S., Wang, S., Mangano, T. J., Deshpande, D. A., Jiang, A., Penn, R. B., Jin, J., Koller, B. H., Kenakin, T., Shoichet, B. K., and Roth, B. L. (2015) Allosteric ligands for the pharmacologically dark receptors GPR68 and GPR65. Nature 527, 477-483
38. Mogi, C., Tomura, H., Tobo, M., Wang, J. Q., Damirin, A., Kon, J., Komachi, M., Hashimoto, K., Sato, K., and Okajima, F. (2005) Sphingosylphosphorylcholine antagonizes proton-sensing ovarian cancer G-protein-coupled receptor 1 (OGR1)-mediated inositol phosphate production and cAMP accumulation. J. Pharmacol. Sci. 99, 160-167
39. Li, J., Guo, B., Wang, J., Cheng, X., Xu, Y., and Sang, J. (2013) Ovarian cancer G protein coupled receptor 1 suppresses cell migration of MCF7 breast cancer cells via a Gα12/13-Rho-Racl pathway. J. Mol. Signal. 8, 6
40. Singh, L. S., Berk, M., Oates, R., Zhao, Z., Tan, H., Jiang, Y., Zhou, A., Kirmani, K., Steinmetz, R., Lindner, D., and Xu, Y. (2007) Ovarian cancer G protein-coupled receptor 1, a new metastasis suppressor gene in prostate cancer. J. Natl. Cancer Inst. 99, 1313-1327
41. Li, B. X. and Xiao, X. (2009) Discovery of a Small-Molecule Inhibitor of the KIX-KID Interaction. Chembiochem 10, 2721-2724
42. Sears, R. C. and Xiao, X. (2015) Identification of a Potent Inhibitor of CREB-Mediated Gene Transcription with Efficacious in Vivo Anticancer Activity. J. Medicial Chem. 58, 5075-5087
43. Ryder, N. M., Guha, S., Hines, O. J., Reber, H. A., and Rozengurt, E. (2001) G protein-coupled receptor signaling in human ductal pancreatic cancer cells: Neurotensin responsiveness and mitogenic stimulation. J. Cell. Physiol. 186, 53-64
44. Guha, S., Eibl, G., Kisfalvi, K., Fan, R. S., Burdick, M., Reber, H., Hines, O. J., Strieter, R., and Rozengurt, E. (2005) Broad-Spectrum G Protein-Coupled Receptor Antagonist, [D-Arg1,D-Trp5,7,9,Leu11]SP: a dual inhibitor of growth and angiogenesis in Pancreatic Cancer. Cancer Res. 65, 2738-2745

45. Matsuo, Y., Raimondo, M., Woodward, T. A., Wallace, M. B., Gill, K. R., Tong, Z., Burdick, M. D., Yang, Z., Strieter, R. M., Hoffman, R. M., and Guha, S. (2009) CXC-chemokine/CXCR2 biological axis promotes angiogenesis in vitro and in vivo in pancreatic cancer. Int. J. Cancer 125, 1027-1037

46. Arafat, H. A., Gong, Q., Chipitsyna, G., Rizvi, A., Saa, C. T., and Yeo, C. J. (2007) Antihypertensives as Novel Antineoplastics: Angiotensin-I-Converting Enzyme Inhibitors and Angiotensin II Type 1 Receptor Blockers in Pancreatic Ductal Adenocarcinoma. J. Am. Coll. Surg. 204, 996-1005

47. Insel, P. A., Wilderman, A., Zambon, A., Snead, A., Murray, F., Aroonsakool, N., McDonald, D., Zhu, S., McCann, T., Zhang, L., Sriram, K., Chinn, A., Michkov, A. V, Lynch, R., Overland, A., and Corriden, R. (2015) GPCR Expression in Native Cells: "Novel" endoGPCRs as Physiologic Regulators and Therapeutic Targets. Mol. Pharmacol. 88, 181-187

48. Uhlén, M., Fagerberg, L., Hallstram, B. M., Lindskog, C., Oksvold, P., Mardinoglu, A., Sivertsson, A., Kampf, C., Sjastedt, E., Asplund, A., Olsson, I., Edlund, K., Lundberg, E., Navani, S., Szigyarto, C. A., Odeberg, J., Djureinovic, D., Takanen, J. O., Hober, S., Alm, T., Edqvist, P., Berling, H., Tegel, H., Mulder, J., Rockberg, J., Nilsson, P., Schwenk, J. M., Hamsten, M., Feilitzen, K. Von, Forsberg, M., Persson, L., Johansson, F., Zwahlen, M., Heijne, G. Von, Nielsen, J., and Pontén, F. (2015) Tissue-based map of the human proteome. Science 347, 1260419-1260419

49. Segerstolpe, Å., Palasantza, A., Eliasson, P., Andersson, E.-M., Andréasson, A.-C., Sun, X., Picelli, S., Sabirsh, A., Clausen, M., Bjursell, M. K., Smith, D. M., Kasper, M., Ammala, C., and Sandberg, R. (2016) Single-Cell Transcriptome Profiling of Human Pancreatic Islets in Health and Type 2 Diabetes. Cell Metab. 24, 593-607

50. Huang, Y., Fan, J., Yang, J., and Zhu, G. Z. (2008) Characterization of GPR56 protein and its suppressed expression in human pancreatic cancer cells. Mol. Cell. Biochem. 308, 133-139

51. Ke, N., Sundaram, R., Liu, G., Chionis, J., Fan, W., Rogers, C., Awad, T., Grifman, M., Yu, D., Wong-Staal, F., and Li, Q.-X. (2007) Orphan G protein-coupled receptor GPR56 plays a role in cell transformation and tumorigenesis involving the cell adhesion pathway. Mol. Cancer Ther. 6, 1840-1850

52. Zhou, H. and Rigoutsos, I. (2014) The emerging roles of GPRC5A in diseases. Oncoscience 1, 765-776

53. Li, M., Wang, X., Li, W., Li, F., Yang, H., Wang, H., Brunicardi, F. C., Chen, C., Yao, Q., and Fisher, W. E. (2010) Somatostatin Receptor-1 Induces Cell Cycle Arrest and Inhibits Tumor Growth in Pancreatic Cancer. 99, 2218-2223

54. Duluc, C., Moatassim-Billah, S., Chalabi-Dchar, M., Perraud, A., Samain, R., Breibach, F., Gayral, M., Cordelier, P., Delisle, M.-B., Bousquet-Dubouch, M.-P., Tomasini, R., Schmid, H., Mathonnet, M., Pyronnet, S., Martineau, Y., and Bousquet, C. (2015) Pharmacological targeting of the protein synthesis mTOR/4E-BP1 pathway in cancer-associated fibroblasts abrogates pancreatic tumour chemoresistance. EMBO Mol. Med. 7, 735-753

55. Walter, K; Omura, N; Hong, S; Griffith, M and Goggins, M. (2008) Pancreatic cancer associated fibroblasts display normal allelotypes. Cancer Biol. Ther. 141, 520-529

56. Pilon-Thomas, S., Kodumudi, K. N., El-Kenawi, A. E., Russell, S., Weber, A. M., Luddy, K., Damaghi, M., Wojtkowiak, J. W., Mul, J. J., Ibrahim-Hashim, A., and Gillies, R. J. (2016) Neutralization of tumor acidity improves antitumor responses to immunotherapy. Cancer Res. 76, 1381-1390

57. Okada, S., Okusaka, T., Ishii, H., Kyogoku, A., Yoshimori, M., Kajimura, N., Yamaguchi, K., and Kakizoe, T. (1998) Elevated serum interleukin-6 levels in patients with pancreatic cancer. Jpn. J. Clin. Oncol. 28, 12-15

58. Lesina, M., Kurkowski, M. U., Ludes, K., Rose-John, S., Treiber, M., Klppel, G., Yoshimura, A., Reindl, W., Sipos, B., Akira, S., Schmid, R. M., and Algl, H. (2011) Stat3/Socs3 Activation by IL-6 Transsignaling Promotes Progression of Pancreatic Intraepithelial Neoplasia and Development of Pancreatic Cancer. Cancer Cell 19, 456-469

59. Bellone, G., Carbone, A., Smirne, C., Scirelli, T., Buffolino, A., Novarino, A., Stacchini, A., Bertetto, O., Palestro, G., Sorio, C., Scarpa, A., Emanuelli, G., and Rodeck, U. (2006) Cooperative induction of a tolerogenic dendritic cell phenotype by cytokines secreted by pancreatic carcinoma cells. J. Immunol. 177, 3448-3460

60. Rhim, A. D., Oberstein, P. E., Thomas, D. H., Mirek, E. T., Palermo, F., Sastra, S. A., Dekleva, E. N., Saunders, T., Becerra, C. P., Tattersall, I. W., Westphalen, C. B., Kitajewski, J., Fernandez-barrena, M. G., Fernandez-zapico, M. E., Iacobuzzio-donahue, C., Olive, K. P., and Stanger, B. Z. (2014) Stromal elements act to restrain, rather than support, pancreatic ductal adenocarcinoma. Cancer Cell 25, 735-747

61. Ozdemir, B. C., Pentcheva-Hoang, T., Carstens, J. L., Zheng, X., Wu, C.-C., Simpson, T., Laklai, H., and Sugimoto, H. (2014) Depletion of Carcinoma-Associated Fibroblasts and Fibrosis Induces Immunosuppression and Accelerates Pancreas Cancer with Diminished Survival. Cancer Cell 25, 719-734

62. Öhlund, D., Santana, A. H., Biffi, G., Elyada, E., Almeida, A. S., Sarvise, M. P., Corbo, V., Oni, T. E., Hearn, S. A., Lee, E. J., In, I., Chio, C., Hwang, C. I1, Tiriac, H., Baker, L. A., Engle, D. D., Feig, C., Kultti, A., Egeblad, M., Fearon, D. T., Crawford, J. M., Clevers, H., Park, Y., and Tuveson, D. A. (2017) Distinct populations of inflammatory fibroblasts and myofibroblasts in pancreatic cancer. J. Exp. Med. 214, 579-596

63. Southan, C., Sharman, J. L., Benson, H. E., Faccenda, E., Pawson, A. J., Alexander, S. P., Buneman, O. P., Davenport, A. P., McGrath, J. C., Peters, J. A., Spedding, M., Catterall, W. A., Fabbro, D., Davies, J. A. and NC-IUPHARM (2016) The IUPHAR/BPS Guide to PHARMACOLOGY in 2016: towards curated quantitative interactions between 1300 protein targets and 6000 ligands. Nucleic Acids Res. 44, D1054-1068

64. Li, B. and Dewey, C. N. (2011) RSEM: accurate transcript quantification from RNA-Seq data with or without a reference genome. BMC Bioinformatics 12:323

65. Vivian, J., Rao, A. A., Nothaft, F. A., Ketchum, C., Armstrong, J., Novak, A., Pfeil, J., Narkizian, J., Deran, A. D., Musselman-Brown, A., Schmidt, H., Amstutz, P., Craft, B., Goldman, M., Rosenbloom, K., Cline, M., O'Connor, B., Hanna, M., Birger, C., Kent, W. J., Patterson, D. A., Joseph, A. D., Zhu, J., Zaranek, S., Getz, G., Haussler, D., and Paten, B. (2017) Toil enables reproducible, open source, big biomedical data analyses. Nat. Biotechnol. 35, 314-316

The invention claimed is:

1. A method for detecting and treating pancreatic cancer in a patient comprising:
    obtaining a biological sample comprising pancreatic tissue or pancreatic cancer associated fibroblasts from the patient;
    detecting expression level of GPR68 in the sample;
    determining that the expression level of GPR68 is greater than in a normal patient sample; and
    treating the patient for pancreatic cancer by inhibiting GPR68 in the patient.

2. The method of claim 1, wherein the expression level is detected by measuring RNA.

3. The method of claim 1, wherein the expression level is detected by measuring protein.

4. The method of claim 1, wherein the sample comprises pancreatic tissue or pancreatic cancer associated fibroblasts.

5. The method of claim 1, wherein the treating inhibits GPR68 expression and/or activity.

6. The method of claim 5, wherein the inhibition includes blocking the ability of low pH to activate GPR68.

7. The method of claim 5, wherein the inhibition includes promotion of an increase in cAMP formation and action.

8. The method of claim 1, wherein the detecting step also includes detecting expression levels of one or more GPCR selected from OXTR, GPR56, GPRC5A, BDKRB1, PPYR1, GPR37, BDKRB2, ADRB2, F2RL1, EDG1, GPR51, FZD4, GPR150, and F2RL2 in the sample.

* * * * *